United States Patent [19]

James

[11] 3,988,450

[45] Oct. 26, 1976

[54] CEPHALOSPORINS

[75] Inventor: Brian George James, Cranleigh, England

[73] Assignee: Beecham Group Limited, Great Britain

[22] Filed: Mar. 27, 1975

[21] Appl. No.: 562,547

[30] Foreign Application Priority Data

Apr. 10, 1974 United Kingdom............... 15805/74

[52] U.S. Cl.............................. 424/246; 260/239 A; 260/239.1; 260/243 C; 260/326.14 R

[51] Int. Cl.²....................................... C07D 501/24

[58] Field of Search................. 260/243 C; 424/246

[56] References Cited
UNITED STATES PATENTS 3,769,277  10/1973  Long et al....................... 260/243 C
3,849,408  11/1974  Dolfini et al.................... 260/243 C

*Primary Examiner*—Nicholas S. Rizzo
*Assistant Examiner*—Mary C. Vaughn

[57] ABSTRACT

Cephalosporin analogues of the formula (I):

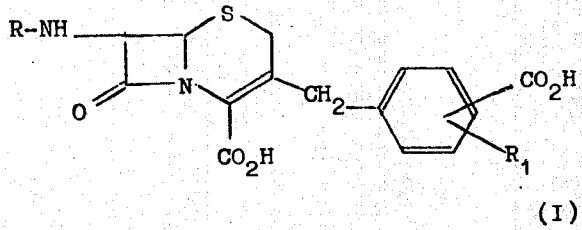

(I)

and their salts and in-vivo hydrolysable esters (wherein R is an acyl group as found in known antibacterially active penicillins and cephalosporins and $R_1$ is a hydrogen atom or a carboxylic acid group) are useful antibacterial agents.

26 Claims, No Drawings

CEPHALOSPORINS

BACKGROUND TO THE INVENTION

Belgian Pat. No. 791,161 discloses inter alia antibacterial agents of the formula (II):

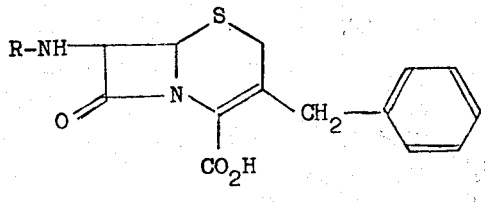

wherein R is an acyl group as found in known antibacterially active penicillins and cephalosporins. It has now been discovered that if the 3-benzyl group of the compounds of formula (II) is replaced by a benzyl group substituted by a carboxylic acid group then many of the resulting compounds have a surprisingly prolonged serum half-life.

DESCRIPTION OF THE INVENTION

The present invention provides cephalosporin analogues of the formula (I):

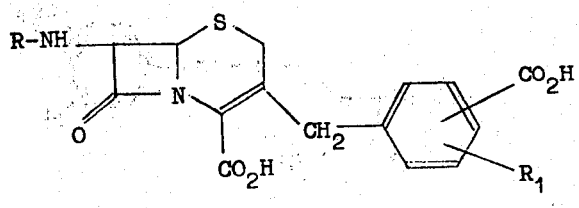

and their salts and in-vivo hydrolysable esters wherein R is an acyl group found in known antibacterially active penicillins and cephalosporins and $R_1$ is a hydrogen atom or a carboxylic acid group.

Both anhydrates and hydrated forms of the compounds of the formula (I) are included in this invention.

In general those compounds wherein $R_1$ is a hydrogen atom are preferred because they tend to have a better level of activity against certain strains of bacteria.

Examples of suitable groups R include those of the sub-formulae (a), (b), (c) and (d):

$$A_1-(CH_2)_n-\underset{X}{CH}-(CH_2)_m-CO \qquad (a)$$

$$A_2-CO \qquad (b)$$

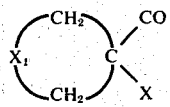 (c)

$$A_1-X_2-(CH_2)_n-CO \qquad (d)$$

wherein n is 0, 1 or 2; m is 0, 1 or 2; $A_1$ is a $C_1$–$C_6$ alkyl, $C_3$–$C_6$ cycloalkyl, cyclohexenyl, cyclohexadienyl, phenyl, substituted phenyl, thienyl or pyridyl group; X is a hydrogen or halogen atom, a carboxylic acid, carboxylic ester, azido, tetrazolyl, hydroxy, acyloxy, amino, ureido, guanidino or acylureido group; $A_2$ is a bulky aromatic group such as a 2,6-dimethoxyphenyl, 2-alkoxy-1-naphthyl or 3-arylisoxazolyl or 3-aryl-5-methylisoxazolyl group; $X_1$ is a $CH_2OCH_2$, $CH_2SCH_2$ or $(CH_2)_n$ group; and $X_2$ is an oxygen or sulphur atom.

A particularly suitable sub-group of the compounds of formula (i) are those of formula (III):

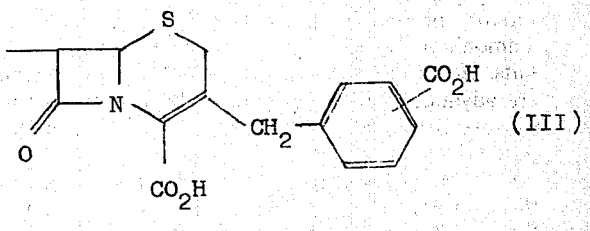

and their salts and in-vivo hydrolysable esters wherein $R_2$ is a 2-thienyl, 3-thienyl or optionally substituted phenyl group of the formula $C_6H_3Z_1Z_2$ wherein $Z_1$ is a hydrogen atom or a hydroxy group and $Z_2$ is a hydrogen or chlorine atom or a hydroxyl or methoxyl group; and $R_3$ is a hydrogen atom or an amino or hydroxyl group or a group of the sub-formulae (e), (f), (g) or (h):

$$CO_2A_3 \qquad (e)$$

$$NH-CO-NA_4-CO-A_5 \qquad (f)$$

$$NH-CO-N(CH_3)-N=A_6 \qquad (g)$$

$$NH-CO-CH(A_7)-NH-A_8 \qquad (h)$$

wherein $A_3$ is a hydrogen atom or an alkyl or alkenyl group of up to 6 carbon atoms or a benzyl, phenyl, toluyl or indanyl group; $A_4$ is a hydrogen atom or a methyl group; $A_5$ is an alkyl or an alkenyl group of up to 6 carbon atoms or such a group substituted by a phenyl group; $A_6$ is a hydrocarbon group of up to 8 carbon atoms; $A_7$ is a group such that HO.CO.-CHA$_7$.NH$_2$ is a naturally occurring amino acid; and $A_8$ is a hydrogen atom or a CO.NH$_2$ or C(NH)NH$_2$ group.

Most suitably $R_3$ is a hydroxyl group or an amino group.

A group of compounds which in our hands have shown a tendency to produce extended blood levels after administration include those of the formula (IV)

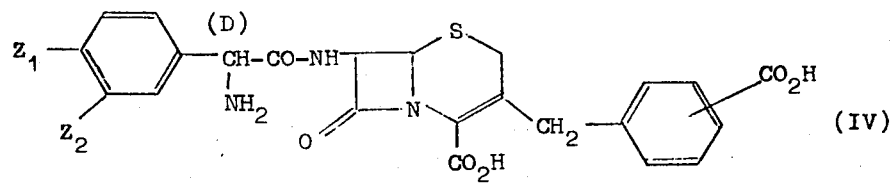
(IV)

and salts thereof wherein $Z_1$ and $Z_2$ are as defined in relation to formula (III).

Preferably $Z_2$ is a hydrogen atom.

We have preferred to use the compounds of formula (IV) wherein $Z_1$ is a hydrogen atom.

When used in relation to formulae (I), (III) or (IV) the term "salt" includes acid addition salts of those compounds containing amino groups as well as salts of the various carboxylic acid groups. Such salts are preferably pharmaceutically acceptable salts such as the sodium, potassium, calcium, magnesium, aluminium, ammonium and conventional substituted ammonium salts. However since the compounds of this invention are advantageously administered by injection or infusion we believe the sodium and potassium salts to be particularly useful.

Examples of suitable in-vivo hydrolysable esters of the compounds of this invention include those which break down readily in the human body to leave the parent acid e.g. acyloxyalkyl esters such as acetoxymethyl, pivaloyloxymethyl, α-acetoxyethyl, α-acetoxybenzyl and α-pivaloyloxyethyl esters. Other suitable esters include lactone, thiolactone and dithiolactone esters of the sub-formula (i):

wherein $Q_1$ and $Q_2$ are oxygen or sulphur and $Q_3$ is a divalent hydrocarbon group, especially the phthalidyl and substituted phthalidyl esters such as the 6,7-dimethoxyphthalidyl ester.

In addition to the above esters the benzylic carboxylic acid group may be esterified by less complex moieties, for example those notionally derived from $C_1$–$C_6$ alkanols, benzylalcohol and the like. The following reaction scheme outlines a method of preparation of compounds of this invention:

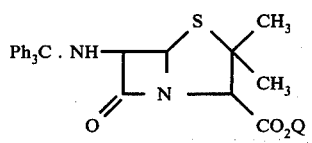

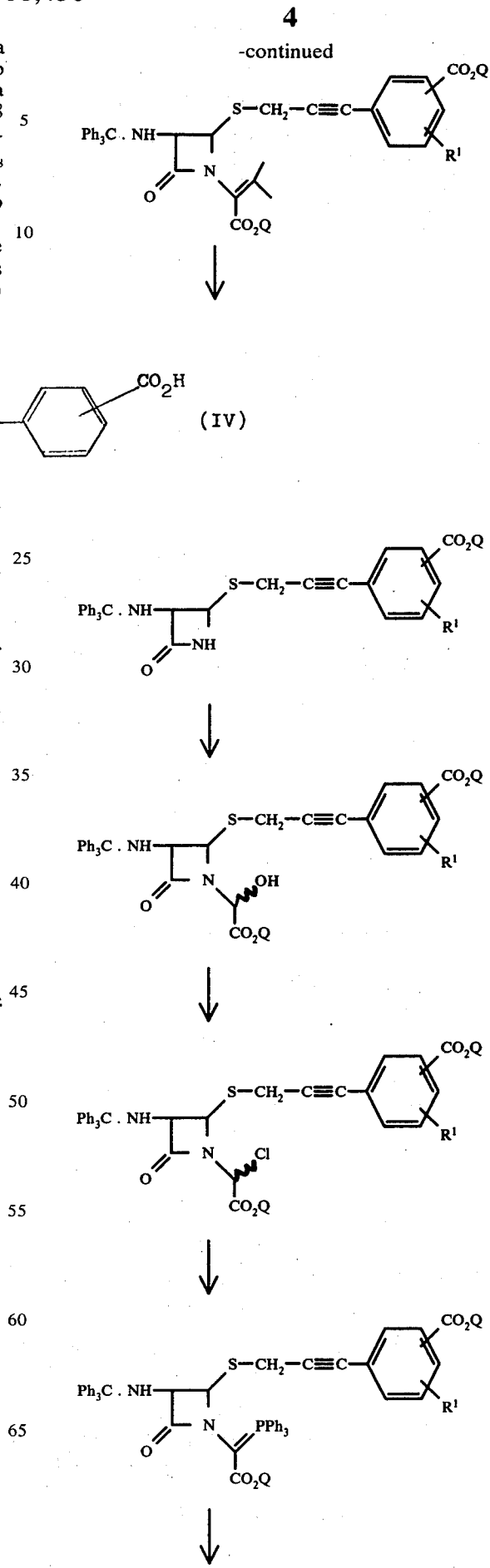

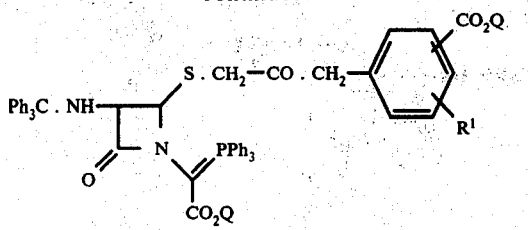

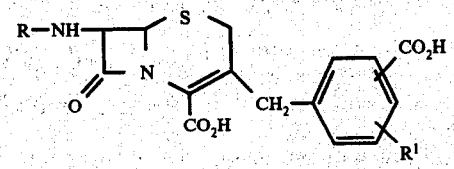

In this reaction scheme the groups $CO_2Q$ are any conventional protected carboxyl groups and the group $R^1$ is a hydrogen atom or a group $CO_2Q$.

The compounds of formula (I) may be prepared by the acylation of a compound of the formula (V):

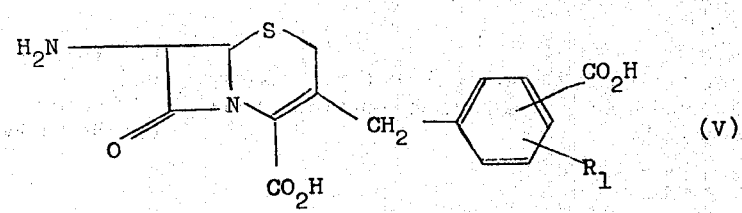

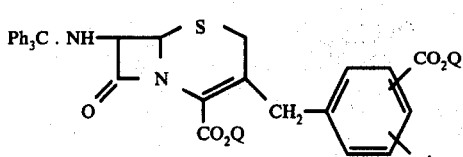

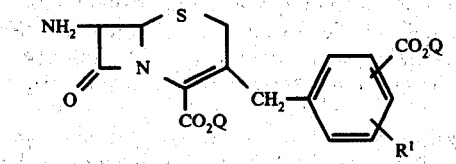

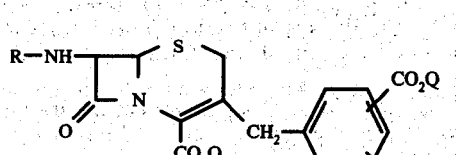

or a salt, ester or silyl derivative thereof with an N-acylating derivative notionally derived from the appropriate acid ROH in which any reactive group optionally present is blocked and thereafter if necessary carrying out one or more of the following steps: (i) removal of any silyl groups by alcoholysis or hydrolysis; (ii) removal of any blocking groups in the acyl side chain R; (iii) converting an esterified carboxylic acid group to a free acid group or salt thereof.

By the term "silyl derivative" of compound (V) we mean the product of the reaction between compound (V) and a silylating agent such as a halodialkylsilane, a halotrialkylsilane, a halodialkoxysilane or a halotrialkoxysilane, or a corresponding aryl or aralkylsilane and compounds such as hexamethyldisilane. The silyl derivatives of compound (V) are extremely sensitive to moisture and hydroxylic compounds, and, after reaction with the N-acylating derivatives of the acid ROH, the silyl groups of the intermediate acylated compound can be removed by alcoholysis or hydrolysis.

Suitable N-acylating derivatives of the acid ROH include the acid chloride, bromide, anhydride, mixed anhydrides and the reactive intermediates formed from the acid and a carbodiimide or a carbonyldiimidazole. Any reactive groups such as amino groups or hydroxy groups which are present in the acyl group R may be protected during the course of the N-acylation. Suitable protecting groups for amino groups are known from the literature on the synthesis of α-aminobenzyl penicillin or α-aminobenzyl cephalosporins. For example, any amino groups may be blocked by protonation, by conversion to tertbutoxycarbonylamino groups or to N-methoxycarbonylpropen-2-ylamino groups. Such protecting groups may subsequently be removed to leave the free amino group. A useful way of protecting a free hydroxy group is to use the appropriate o-carboxylic anhydride such as mandelic o-carboxyanhydride. After N-acylation with this reagent the free hydroxy group is generated without the need for de-protection.

The compounds of the formula (V) and their salts, esters and silyl derivatives are novel and useful intermediates and as such form a useful aspect of the present invention.

One particularly useful group of intermediates of the formula (V) are those of the formula (VI):

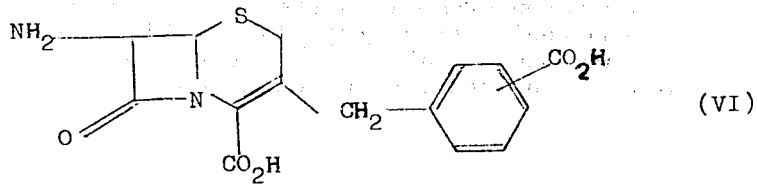

(VI)

and esters thereof.

The compound of the formula (V) or their esters may be prepared from a corresponding compound of the formula (VII):

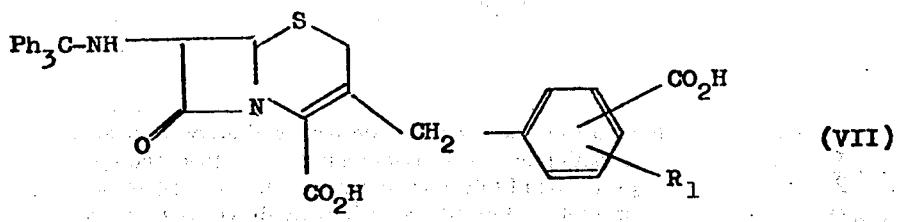

(VII)

or ester thereof by treatment with an acid such as p-toluene-sulphonic acid at a depressed temperature, for example, $-20°$ C $- 0°$ C. Such reactions are generally carried out in an organic solvent such as methanol.

Silyl derivatives of the compounds of the formula (V) may be prepared from the corresponding compound of formula (V) in conventional manner in which the carboxyl groups are esterified using reaction conditions such as those described in Belgian Pat. No. 783,298.

The compounds of the formula (VII) may in general be prepared by heating a compound of the formula (VIII):

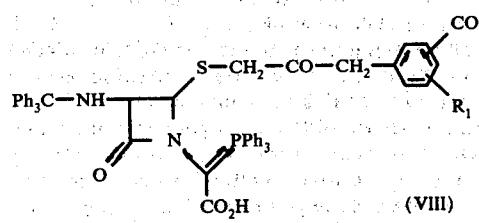

(VIII)

in which each of the carboxylic acid groups are esterified.

Such reactions are best carried out in an inert organic solvent such as dry dioxan or dry tetrahydrofuran or the like at a temperature of at least 50° C, for example, by heating the mixture under reflux.

The compounds of the formula (VIII) may be obtained by hydration of the corresponding compound of the formula (IX):

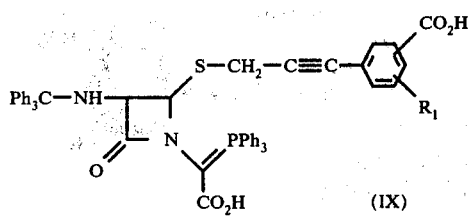

(IX)

in which each of the carboxylic acid groups are esterified.

The compound of formula (IX) may be prepared as described in the specific examples herein and by analogous process as described in Belgian Patent No. 783,298.

In a further aspect this invention provides an antibacterial pharmaceutical composition which comprises a compound of the formula (I) as hereinbefore defined together with a pharmaceutically acceptable carrier.

A particularly suitable form of this aspect of the invention comprises an injectable composition containing a compound of the formula (IV) as hereinbefore defined, especially those compounds of formula (IV) wherein $Z_3$ is an amino group and $Z_2$ is a hydrogen atom.

As previously stated compounds of formula (IV) show the tendency to possess prolonged blood levels after administration. These blood levels are such that the compound need be administered only 2 or 3 times daily in place of the usual 4 times daily. A favoured aspect of this invention provides a method of treating bacterial infections in mammals including humans which comprises the administration of up to three daily doses of a compound of the formula (IV) or salt thereof.

Generally a unit dose of a compound of this invention is from 100 mg to 4 g, more usually 125 mg to 1 g and normally 200 mg to 600 mg.

The following Examples illustrate the preparation of some of the compounds of this invention.

EXAMPLE 1

(a) Preparation of t-Butyl 3-[p-(p-methoxybenzyloxycarbonyl)benzyl]-7β-(N-t-butoxycarbonyl-D-α-phenylglycyl)amino-ceph-3-em-4-carboxylate (XII)

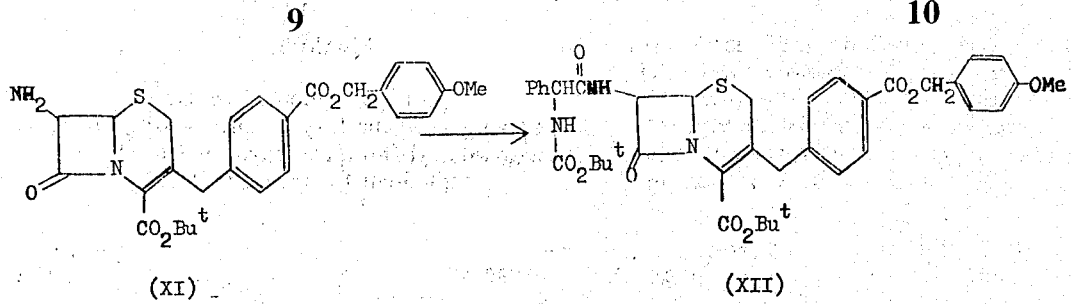

(XI)    (XII)

A solution containing triethylamine (54 mg.), N-(t-butoxycarbonyl)-D-α-phenylglycine (135 mg.) and N,N-dimethylbenzylamine (1 microdrop) in dry tetrahydrofuran (2 ml.) was added dropwise over 5 minutes to a stirred solution of methyl chloroformate (50 mg.) in dry tetrahydrofuran (1 ml.) at −20°. The mixture was stirred for a further 0.5 hr. at −20° before a solution of the amino cephem (XI) (250 mg.) in dry tetrahydrofuran (2 ml.) was added dropwise over 5 minutes. After stirring for a further 2 hr. at −20° the tetrahydrofuran was removed in vacuo. The residue was dissolved in ethyl acetate and the organic layer washed successively with dilute hydrochloric acid (0.25 N, 2×10 ml.), water, and saturated sodium bicarbonate solution. Evaporation of the dried ethyl acetate layer and chromatography of the residue on silica gel, eluting with ethyl acetate/petroleum ether mixtures gave the cephem (XII) (193 mg., 54%) as a solid m.p. 152°–154°.

$\nu_{max}$ (CHCl$_3$) 3400, 1785, 1710 cm$^{-1}$. δ ppm (CDCl$_3$) 1.38 (s, 9H), 1.52 (s, 9H), 2.88 and 3.32 (ABq, 2H, J=18Hz.), 3.44 and 4.08 (ABq., 2H, J=15Hz.), 3.8 (s, 3H), 4.90 (d, 1H, J=5Hz.), 5.18 (d, 1H, J=6Hz.), 5.30 (s, 2H), 5.65 (d, 1H, J=6H, NH), 5.80 (dd, 1H, J=5, 10Hz.), 6.8 (d, 1H, J=10Hz.,NH), 6.90 (d, 2H, J=9Hz.), 7.15–7.5 (m, 9H), 8.0 (d, 2H, J=9Hz.). (Found: C, 64.61; H, 6.29; N, 5.33; S, 4.02%. C$_{40}$H$_{45}$N$_3$O$_9$S requires: C, 64.60; H, 6.05; N, 5.65; S, 4.30%).

(b) Preparation of 3-(p-Carboxybenzyl)-7β-(D-α-phenylglycyl)aminoceph-3-em-4-carboxylic acid trifluoroacetic acid salt (XIII)

The cephem (XII) (86 mg.) was dissolved in trifluoroacetic acid (0.05 ml.) and the solution was kept at room temperature for 10 minutes. The solution was evaporated and the residual gum re-evaporated from dry toluene (3×5 ml.). The residual gum was triturated with dry ether to give the desired trifluoroacetic acid salt (XIII) (63 mg., 93%) as a solid. $\nu_{max}$ (Nujol) 2300–2700, 1770, 1690 cm$^{-1}$.

The minimum inhibition concentrations (MIC) of this compound required to inhibit the growth of various bacteria on nutrient agar are tabulated below:

| Gram-positive bacteria | MIC (µg/ml) |
| --- | --- |
| B. subtilis | 1.25 |
| Staph. aureus Oxford | 0.5 |
| Staph. aureus Russell | 2.5 |
| β-Haemolytic Strep. CN10 | 0.5 |
| Gram-negative bacteria | |
| E. coli JT1 | 12.5 |
| Salmonella typhi | 0.5 |
| Shigella sonnei | 5.0 |
| Proteus mirabilis C977 | 1.25 |

EXAMPLE 2

(a) Preparation of t-Butyl 3-[p-(p-methoxybenzyloxycarbonyl)benzyl]-7β-(D-mandelyl)amino-ceph-3-em-4-carboxylate (XIV)

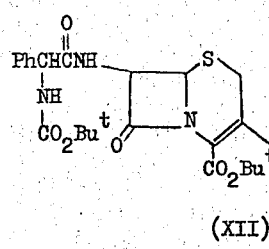 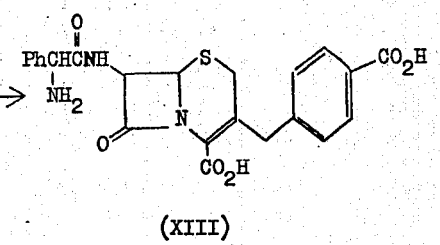

(XII)    (XIII)

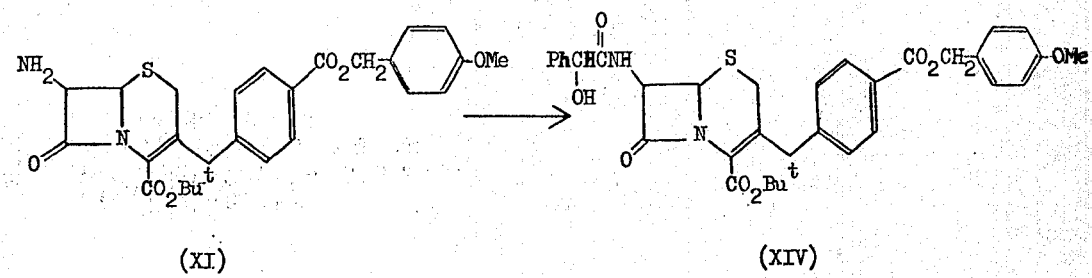

(XI)    (XIV)

D-Mandelyl O-carboxyanhydride (195 mg.) was added to a stirred solution of the amino cephem (XI) (250 mg.) in dry methylene chloride (20 ml.) at −20°. The mixture was stirred for 1 hr. at −20° and the solvent was removed in vacuo. Chromatography of the residue on silica gel eluting with ethyl acetate-

EXAMPLE 3

(a) Preparation of t-Butyl 3-[p-(p-methoxybenzyloxycarbonyl)benzyl]-7β-(N-t-butoxycarbonyl-D-α-p-hydroxyphenylglycyl)amino-ceph-3-em-4-carboxylate. (XVI)

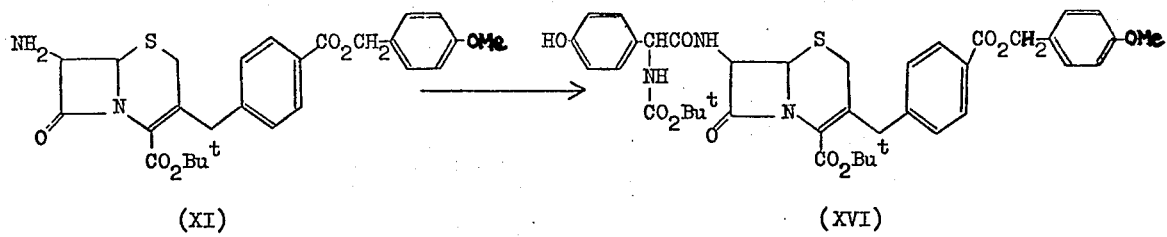

(XI)                                (XVI)

petroleum ether mixtures gave the cephem (XIV) 304 mg., 94%) as a crisp foam.

$\nu_{max}$ (CHCl$_3$) 3400, 1790, 1720 1700 (sh) cm$^{-1}$. δ ppm (CDCl$_3$) 1.55 (s, 9H), 2.95 and 3.38 (ABq, 2H, J=18Hz.), 3.5 and 4.14 (ABq, 2H, J=15Hz.), 3.76 (s, 1H, exchanges with D$_2$O), 3.85 (s, 3H), 4.96 (d, 1H, J=5Hz.), 5.12 (s, 1h), 5.34 (s, 2H), 5.75 (dd, 1H, J=5, 10Hz.), 6.94 (d, 2H, J=9Hz.), 7.08 (d, 1H, J=10Hz., NH), 7.2–7.6 (m, 9H), 8.04 (d, 2H, J=9Hz.).

(b) Preparation of
3-(p-Carboxybenzyl-7β-(D-mandelyl)amino-ceph-3-em-4-carboxylic acid (XV)

A solution containing triethylamine (54 mg.), N-(t-butoxycarbonyl)-D-α-p-hydroxyphenylglycine (145 mg.) and N,N-dimethylbenzylamine (1 microdrop) in dry tetrahydrofuran (2 ml.) was added dropwise over five minutes to a stirred solution of methyl chloroformate (50 mg.) in dry tetrahydrofuran (1 ml.) at −20°. The mixture was stirred for a further 0.5 hr. at −20° before a solution of the aminocephem (XI) (250 mg.) in dry tetrahydrofuran (2 ml.) was added dropwise over 5 minutes. After stirring for a further 2 hr. at −20° the tetrahydrofuran was removed in vacuo. The residue was dissolved in ethyl acetate and the organic layer was washed successively with dilute hydrochloric acid

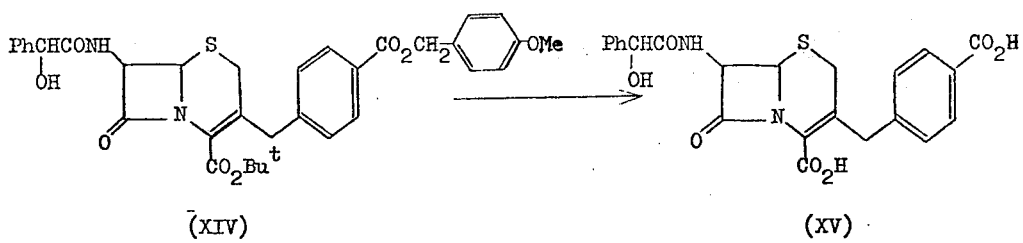

(XIV)                                (XV)

The cephem (XIV) (195 mg.) was dissolved in trifluoroacetic acid (1 ml.) and the solution was kept at room temperature for 20 minutes. The solution was evaporated and the residual gum re-evaporated from dry toluene (3×5 ml.). The residual gum was triturated with chloroform to give the desired decarboxylic acid (XV) (140 mg. 98%). $\nu_{max}$ (Nujol) 2300-3500 (br), 1770, 1720, 1690 cm$^{-1}$.

The minimum inhibitory concentrations (MIC) of this compound require to inhibit the growth of various bacteria on nutrient agar are tabulated below:

| Gram-positive bacteria | MIC (μg/ml) |
|---|---|
| B. subtilis | 0.5 |
| Staph. aureus Oxford | 0.25 |
| β-Haemolytic Strep. CN10 | 0.25 |
| Gram-negative bacteria | |
| E. coli JT1 | 5.0 |
| Salmonella typhi | 5.0 |
| Proteus mirabilis C977 | 0.5 |

(0.25 N), water, and sodium bicarbonate solution. Evaporation of the dried ethyl acetate layer and chromatography of the residue on silica gel, eluting with ethylacetate-petroleum ether mixtures gave the cephem (XVI) (220 mg., 58%) as a foam.

$\nu_{max}$ (CHCl$_3$) 3400, 1780, 1710, 1680 (sh) cm$^{-1}$. δ ppm (CDCl$_3$) 1.40 (s, 9H), 1.52 (s, 9H), 1.95 (s, 1H, exchanges with D$_2$O), 2.88 and 3.38 (ABq., 2H, J=18Hz.), 3.48 and 4.1 (ABq, 2H, J=16Hz.), 3.82 (s, 3H) 4.95 (d, 1H, J=5Hz.), 5.1 (d, 1H, J=6Hz.), 5.32 (s, 2H). 5.72 (d, 1H, J=6Hz., NH), 5.80 (dd, 1H, J=6, 10Hz.), 6.5-7.5 (m, 11H), 7.98 (d, 2H, J=9Hz.).

(b) Preparation of
3-(p-carboxybenzyl)-7β-(D-α-p-hydroxyphenylglycyl-)aminoceph-3-em-4-carboxylic acid trifluoroacetic acid salt (XVII)

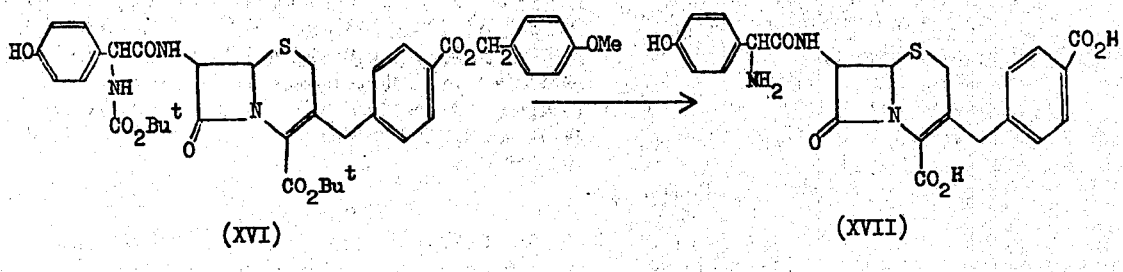

(XVI) → (XVII)

The cephem (XVI) (115 mg) was dissolved in trifluoroacetic acid (0.5 ml.) and the solution was kept at room temperature for 10 minutes. The solution was evaporated and the residual gum re-evaporated from dry toluene (3×5 ml.). The residual gum was triturated with dry ether to give the desired trifluoroacetic acid salt of the cephem (XVII) (68 mg., 77%). $\nu_{max}$ (Nujol) 2500–3300, 1770, 1680 (br) cm$^{-1}$.

The minimum inhibitory concentrations (MIC) of this compound required to inhibit the growth of various bacteria on nutrient agar are tabulated below:

| Gram-positive bacteria | MIC (μg/ml) |
|---|---|
| B. subtilis | 5.0 |
| Staph. aureus Oxford | 2.5 |
| Staph aureus Russell | 5.0 |
| β-Haemolytic Strep. CN10 | 0.5 |

| Gram-negative bacteria | MIC (μg/ml) |
|---|---|
| Salmonella typhi | 5.0 |
| Proteus mirabilis C977 | 2.5 | dry benzene (150 ml.). The reaction mixture was stirred, and the resulting exothermic reaction was controlled by external cooling to ensure that the reaction temperature did not exceed 40°–45°. Evaporation of the clear solution, after 10 minutes, gave an oil which was chromatographed on silica gel, eluting with ethyl acetate-petroleum ether (3:7), to give the bromide (II) (36 g., 90%) as a solid, which recrystallised from ethyl acetate-petroleum ether as needles m.p. 60°, $\nu_{max}$ (CHCl$_3$) 1720, 1610, 1590, 1520 cm$^{-1}$; δppm (CDCl$_3$) 3.82 (s, 3H), 4.17 (s, 2H), 5.32 (s, 2H), 6.92 (d, 2H, J=9Hz.), 7.46 (d, 2H, J=9Hz.), 7.54 (d, 2H, J=9Hz.), 8.06 (d, 2H, J=9Hz.). (Found: C, 59.80; H, 4.25; Br, 21.71% C$_{18}$H$_{15}$BrO$_3$ requires: C, 60.17; H, 4.18; Br, 22.28%).

(b) Preparation of 1-(1-Benzyloxycarbonyl-2-methyl-1-propenyl)-3-(triphenylmethylamino)-4-[3-p(p-methoxybenzyloxycarbonyl)phenylprop-2-ynylthio]azetidin-2-one. (IV)

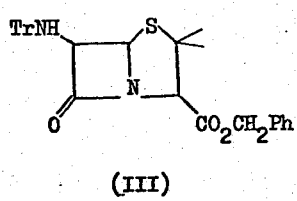

(III)

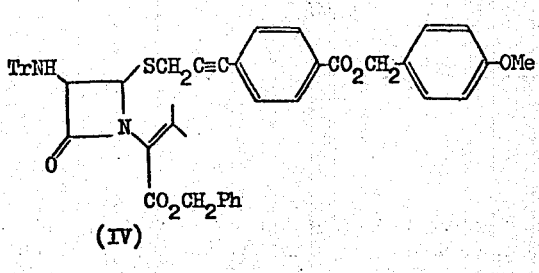

(IV)

PREPARATION OF STARTING MATERIAL FOR EXAMPLES 1, 2 and 3

(a) Preparation of 1-Bromo-[3-p(p-methoxybenzyloxycarbonyl)]phenylprop-2-yne (II)

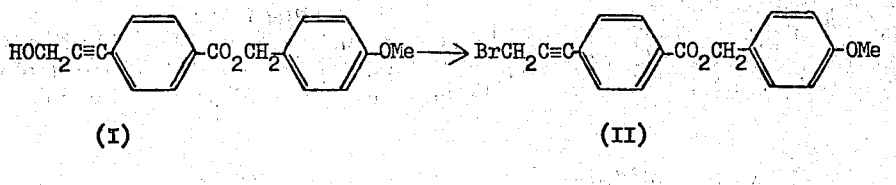

(I) → (II)

Carbon tetrabromide (45 g.) was added to a suspension of triphenylphosphine (33 g.) and 3-p(p-methoxybenzyloxycarbonyl)phenylprop-2-ynol (I) (33 g.) in Benzyl 6-β-(triphenylmethylamino)penicillanate (28 g.) was stirred in dry tetrahydrofuran (250 ml.) containing 1-bromo-[3-p(p-methoxybenzyloxycarbonyl)]-phenylprop-2-yne (II)(20 g.). Freshly powdered sodium hydroxide (2.5 g.) was added, and the mixture was stirred at room temperature for 24 hours. The reaction mixture was diluted with ethyl acetate and the organic layer washed with water and brine. Evaporation of the dried ethyl acetate extract gave a residue which was chromatographed on silica gel, eluting with ethyl acetate-petroleum ether (3:7), to give the product (IV) (26.7 g., 63%) as a foam, $\nu_{max}$ (CHCl$_3$) 1765, 1720 cm$^{-1}$; δ ppm (CDCl$_3$) 2.0 (s,3H), 2.16 (s,3H), 2.93 (centre of AB quartet, 2H, J=18H, covering exchangeable NH signal 1H), 3.8 (s, 3H), 4.53 (broadened, 1H, collapses to doublet, J=5Hz. on D$_2$O exchange), 4.9 (d, 1H, J=5Hz.), 4.98 (centre of AB quartet, 2H, J=12Hz.), 5.32 (s, 2H), 6.94 (d, 2H, J=9Hz.), 7.1-7.7 (m, 24H), 2.1 (d, 2H, J=9Hz.). (Found: C, 75.88; H, 5.70; N, 3.34; S, 3.88%; C$_{52}$H$_{46}$N$_2$O$_6$S requires C, 75.54; H, 5.57; N, 3.39; S, 3.87%).

none (V) (1.1 g., 29%) as a crisp foam, $\nu_{max}$ (CHCl$_3$) 3400, 1762, 1710, 1610cm$^{-1}$; δ $^{ppm\ (CDCl_3)}$ 3.0 (d, 1H, J=9Hz., exchanges with D$_2$O), 3.28 (bs, 2H), 3.82 (s, 3H), 4.62 (m, 2H, collapses to singlet on D$_2$O exchange), 5.34 (s, 2H), 6.26 (bs, 1H, exchanges with D$_2$O), 6.9 (d, 2H, J=9Hz.), 7.1-7.7 (m, 19H), 8.0 (d, 2H, J=9Hz.).

(d) Preparation of 1-(1-Hydroxy-1-t-butoxycarbonylmethyl)-3-(triphenylmethylamino-4-[3-p-(p-methoxybenzyloxycarbonyl)phenylprop-2-ynylthio]azetidin-2-one (VI).

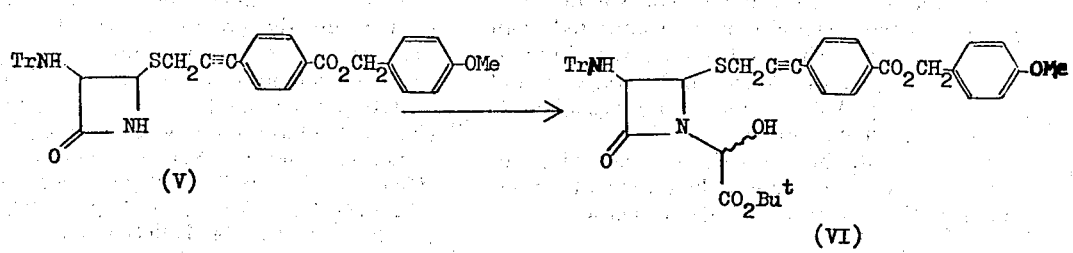

(c) Preparation of 3-(Triphenylmethylamino)-4-[3-p(p-methoxybenzyloxycarbonyl)phenylprop-2-ynylthio]azetidin-2-one. (V)

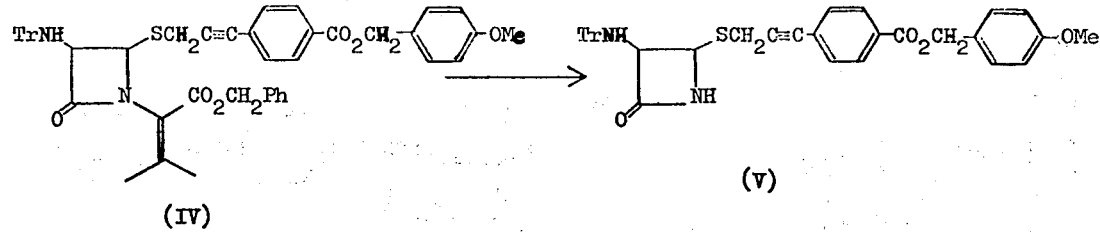

A solution of the azetidinone (V) (13.2 g.) and t-butylgiyoxylate (21 g.) in benzene (250 ml.) was boiled under reflux with provision for the removal of water. After 5 hr. the solution was cooled to room temperature and was washed thoroughly with water (5×100 ml.). Evaporation of the dried benzene solution followed by chromatography of the residue on silica gel, eluting with ethyl acetate-petroleum ether (3:7) gave the alcohols (VI) (11.68 g., 74%) as a foam, $\nu_{max}$ (CHCl$_3$) 3500, 1770, 1730, 1610 cm$^{-1}$; δ ppm (CDCl$_3$) 1.5 (s, 9H), 3.05 (d, 1H, J=9Hz., exchanges with D$_2$O), 3.2 and 3.4 (2s, SCH$_2$ of two isomers), 3.78 (s, 3H), 4.5-4.9 (m, 3H 1H, exchanges with D$_2$O), 5.18 (d, 1H, J=7Hz.), 5.3 (s, 2H), 6.9 (d, 2H, J=9Hz), 7.1-7.6 (m, 19H), 8.02 (d, 2H, J=9Hz.).

A solution of the lactam (IV) (5.0 g.) in dimethyl formamide (15.1 ml.) and pyridine (15.1 ml.) containing water (3.05 ml.) was cooled to −20°. Freshly powdered potassium permanganate (1.43 g.) was added portion wise to the stirred solution at such a rate that the temperature did not exceed 0°. The mixture was stirred for a further 1 hr. at −20° and was then diluted with ethyl acetate (40 ml.) and water (40 ml.). Sulphur dioxide was bubbled through the mixture until two clear layers were produced. The organic phase was washed with 1-N-hydrochloric acid and sodium bicarbonate solution. Evaporation of the dried ethyl acetate solution followed by chromatography of the residue on silica gel, eluting the ethyl acetate-petroleum ether (3:7) gave unchanged (IV) (0.61 g.) and the azetidi- (e) Preparation of 1-(1-Chloro-1-t-butoxycarbonylmethyl)-3-(triphenylmethylamino)-4-[3-p-(p-methoxybenzyloxycarbonyl)-phenylprop-2-ynylthio]azetidin-2-one (VII)

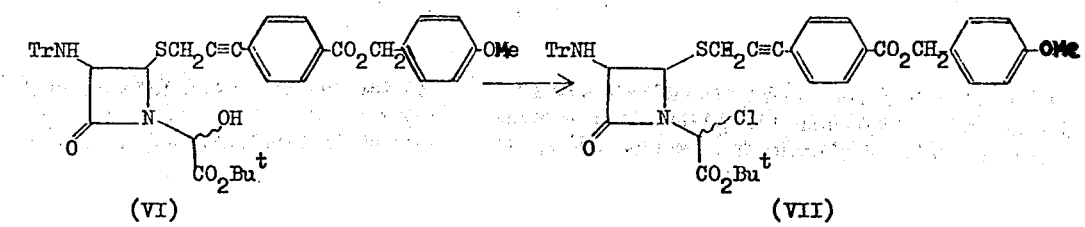

A solution of the lactam (VI) (5 g.) in dry tetrahydrofuran (50 ml.) containing lutidine (2.38 g.) was cooled to −10°. Thionyl chloride (2.32 g.) was added dropwise to the stirred solution over fifteen minutes. After a further 3 minutes the precipitated solid was filtered off and the filtrate evaporated to dryness. Dry toluene was added and the solution was decanted from any solid, and evaporated to give the chloride (VII) (4.0 g.) as a foam. $\nu_{max}$ (CHCl$_3$) 1770, 1730 cm$^{-1}$.

(f) Preparation of 1-(1-t-Butoxycarbonyl-1-triphenylphosphoranylidenemethyl)-3-(triphenylmethylamino)-4-[3-p-(p-methoxybenzyloxycarbonyl)phenylprop-2-ynylthio]azetidin-2-one. (VIII)

A solution of the phosphorane (VIII) (7.86 g.) in piperidine (50 ml.) was stirred at 50° for 4 hr. The piperidine was removed in vacuo and the residue was dissolved in ethyl acetate. The ethyl acetate solution was washed successively with 0.1-N-hydrochloric acid, water and sodium bicarbonate solution. Evaporation of the dried ethyl acetate solution followed by chromatography of the residue on silica gel, eluting with ethyl acetate-petroleum ether mixtures gave the keto-phosphorane (IX) (6.5 g., 82%) as a foam. $\nu_{max}$ (CHCl$_3$) 1750, 1710, 1630, 1610 cm$^{-1}$.

(h) Preparation of t-Butyl 3-[p-(p-methoxybenzyloxycarbonyl)benzyl]-7-triphenylmethylamino-3-ceph-4-carboxylate. (X)

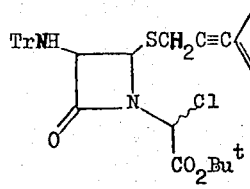

(VII)

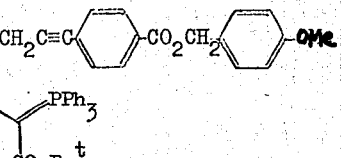

(VIII)

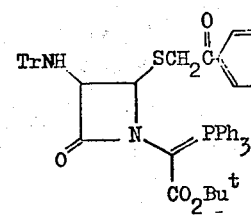

(IX)

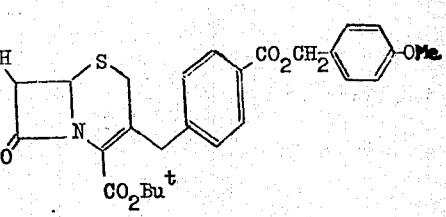

(X)

A solution of the chloride (VII) (4.0 g.) and triphenylphosphine (3.4 g.) in dry dioxan (50 ml.) containing lutidine (3.4 g.) was stirred at 50° under nitrogen for 15 hr. The reaction mixture was filtered and the filtrate evaporated. Chromatography of the residue on silica gel, eluting with ethyl acetate-petroleum ether (3:7) then (1:1) gave the phosphorane (VIII) (4.25 g., 80%) as a crisp foam. $\nu_{max}$ (CHCl$_3$) 1755, 1715, 1635, 1610 cm$^{-1}$.

(g) Preparation of 1-(1-t-Butoxycarbonyl-1-triphenylphosphoranylidenemethyl)-3-(triphenylmethylamino)-4-[3-p-(p-methoxybenzyloxycarbonyl)phenyl-2-oxopropylthio]azetidin-2-one (IX)

A solution of the keto-phosphorane (IX) (6.479 g.) in dioxan (100 ml.), was boiled under reflux for 24 hr. under nitrogen. Evaporation of the solvent and chromatography of the residue on silica gel, eluting with ethyl acetate-petroleum ether (3:7) gave the cephem (X) (3.84 g., 82%) as a solid, which was recrystallised from methanol as needles m.p. 101°–102°. $\nu_{max}$ (CHCl$_3$) 1770, 1720, 1610 cm$^{-1}$. δ ppm (CDCl$_3$) 1.8 (s, 9H), 2.95 (d, 1H, J=10Hz., exchanges with D$_2$O), 2.98 and 3.07 (2H, inner signals of AB quartet), 3.50 and 4.02 (ABq, 2H, J=15Hz.), 3.84 (s, 3H), 4.30 (d, 1H, J=5Hz.), 4.75 (dd, 1H, J=5, 10Hz., collapses to doublet J=5Hz. on D$_2$O exchange), 5.32 (s, 2H), 6.92 (d, 2H, J=9Hz.), 7.15–7.60 (m, 19H), 8.0 (d, 2H, J=19Hz.). (Found: C, 73.38; H, 6.06; N, 3.50; S,

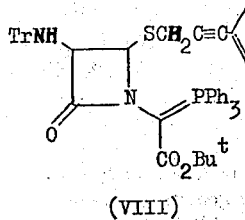

(VIII)

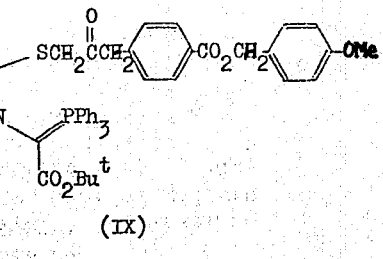

(IX)

4.55%. $C_{46}H_{44}N_2O_6S$ requires: C, 73.40; H, 5.85; N, 3.72; S, 4.25%).

(i) Preparation of t-Butyl 3-[p-(p-methoxybenzyloxycarbonyl)benzyl]-7-amino-3-cephem-4-carboxylate. (XI)

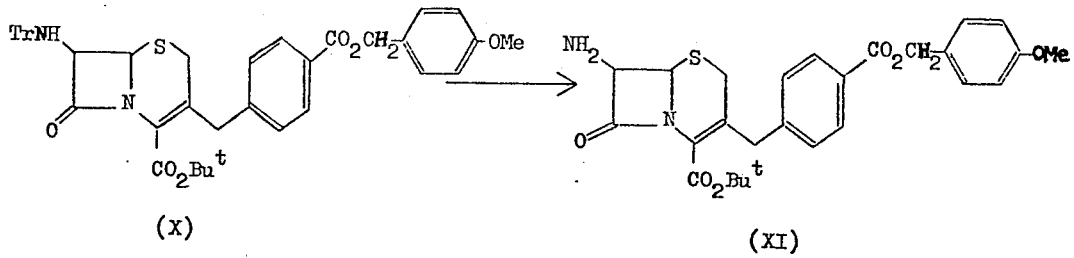

(X)  (XI)

A solution of the cephem (X) (3.8g.) in methylene chloride (10 ml.) was cooled to −20°. A solution of p-toluenesulphonic acid (1.0 g.) in methanol (5 ml.) was added. The solution was left at 0° for 16 hr. and was then washed with sodium bicarbonate solution. Evaporation of the residue with ether gave the free amino cephem (XI) (1.75 g., 68%) as a solid m.p. 134°–135°. $\nu_{max}$ (CHCl$_3$)1775, 1710 cm$^{-1}$. δ ppm (CDCl$_3$) 1.5 (s, 9H), 3.0 and 3.4 (ABq, 2H, J=20Hz.), 3.5 and 4.12 (ABq, 2H, J=15Hz.), 3.83 (s, 3H), 4.71 (d, 1H, J=7Hz.), 4.95 (d, 1H, J=5Hz.), 5.32 (s, 2H), 6.94 (d, 2H, J=9Hz.), 7.25–7.55 (m, 4H), 8.08 (d, 2H, J=9Hz.).

EXAMPLE 4

Preparation of 3-(p-Carboxybenzyl)-7β-[D-α-(3-benzylideneimino-3-methylureido)phenylacetamido]ceph-3-em-4-carboxylic acid (XIX)

triturated with ether, filtered and collected to give (XIX) (0.208 g) as a white solid, $\nu_{max}$ (CHCl$_3$)3320, 1770, 1690 (b) cm$^{-1}$.

The minimum inhibitory concentrations of this compound required to inhibit the growth of various bacteria on nutrient agar are tabulated below:

| Gram-negative bacteria | MIC (μg/ml) |
| --- | --- |
| E. coli JT1 | 12.5 |
| Salm. typhi | 5.0 |
| Shig. sonnei | 2.5 |
| Serratia marcescens US32 | 12.5 |
| Klebsiella aerogenes A | 5.0 |
| Enterobacter cloacae N1 | 5.0 |
| P. mirabilis C977 | 5.0 |
| P. morganii | 12.5 |
| Gram-positive bacteria | |
| Staph. aureus Oxford | 1.25 |
| β-haemolytic strep. CN10 | 0.12 |

EXAMPLE 5

Preparation of 3-(p-Carboxybenzyl)-7β-[D-α-(3-cinnamoyl-3-methylureido)phenylacetamido]ceph-3-em-4-carboxylic acid (XXI)

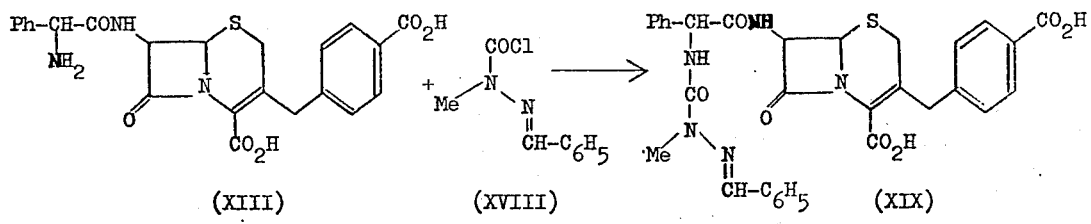

(XIII)  (XVIII)  (XIX)

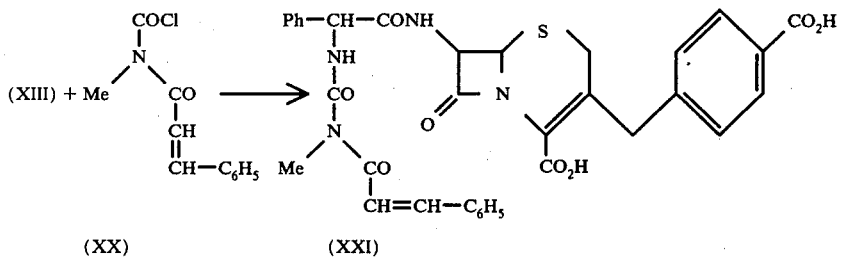

(XX)  (XXI)

The cephem (XIII) (0.25 g as trifluoroacetic acid salt) in methylene chloride (5 ml) was stirred and cooled (ice-bath). Triethylamine (174 mg) was added followed by the carbamoyl chloride (XVIII) (93 mg). After stirring at room temperature for 3 hr the solution was evaporated to dryness. Ethyl acetate and water were added to the residue and the pH adjusted to 2 with N HCl. The ethyl acetate layer was separated, washed with water, dried and evaporated. The residue was The cephem (XIII), (0.25 g of trifluoroacetic acid salt) was treated with triethylamine (174 mg) and the carbamoyl chloride (XX) (106 mg) as in example 4. The product (XXI) (250 mg) was obtained as an amorphous solid, $\nu_{max}$ (mull) 3200, 1770, 1680 (b) cm$^{-1}$.

The minimum inhibitory concentrations (MIC) of this compound required to inhibit the growth of various bacteria on nutrient agar are tabulated below:

| Gram-negative bacteria | MIC (µg/ml) |
|---|---|
| E. coli JT1 | 12.5 |
| Salm. typhi | 12.5 |
| Shig. sonnei | 5.0 |
| Serratia marcescens US32 | 5.0 |
| Klebsiella aerogenes A | 5.0 |
| Enterobacter cloacae N1 | 5.0 |
| P. mirabilis C977 | 5.0 |
| Gram-positive bacteria | |
| Staph. aureus Oxford | 2.5 |
| β-haemolytic strep. CN10 | 0.12 |

α-protons), 5.03 (d, 1H, J=5Hz), 5.20 (s, 2H), 6.20 (dd, 1H, J=9Hz, 5Hz collapsing to d J=5Hz on $D_2O$ exch.), 6.9–8.15 (Ar, NH, 19H). (Found: C, 66.9; H, 5.5; N, 4.0; S, 4.2. $C_{42}H_{40}N_2O_9S$ requires C, 67.4; H, 5.4; N, 3.7; S, 4.3%).

(b) Preparation of 3-(p-Carboxybenzyl)-7β-(DL-α-phenoxycarbonyl-phenylacetamido) ceph-3-em-4-carboxylic acid (XXIV)

(XXIII) ⟶

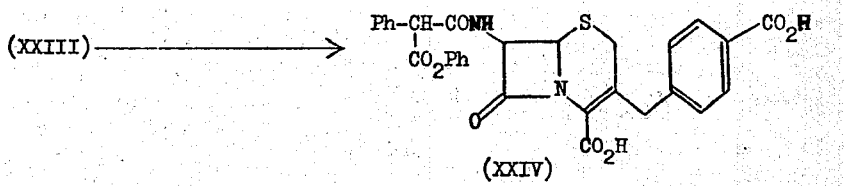

(XXIV)

EXAMPLE 6

(a) Preparation of t-Butyl 3-[p-(p-methoxybenzyloxycarbonyl)benzyl]-7β-[DL-α-phenoxycarbonylphenylacetamido]ceph-3-em-4-carboxylate (XXIII)

The protected cephem (XXIII) (0.1 g) was dissolved in trifluoroacetic acid (2 ml) and left at room temperature for 20 minutes. The solution was evaporated to dryness and then re-evaporated from dry toluene (×2). The residue was triturated with ether and the product (XXIV) (65 mg) was collected and dried, $\lambda_{max}$ (EtOH)

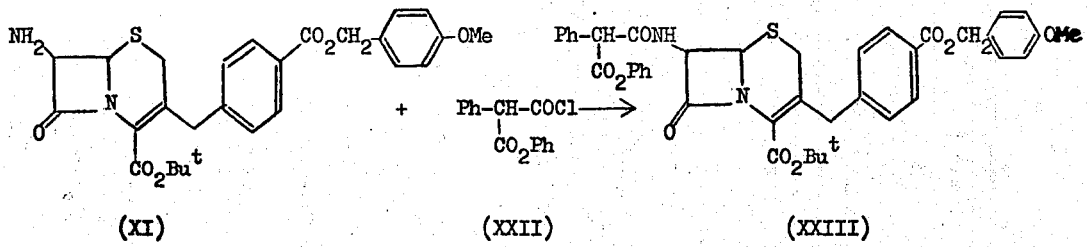

The free base (XI) (0.4g) in methylene chloride (10 ml) was cooled to −10°. Triethylamine (0.16 g) was added followed by the dropwise addition of the acid chloride (XXII) (0.322 g) in methylene chloride. After 40 min at −10° the organic phase was washed with water, dried, and evaporated. The residue was chromatographed on silica gel to give the product (XXIII) (0.42 g), which was crystallised from ether, m.p. 131°–132°, $\nu_{max}$ (EtOH) 227 (λ 20,100), 265 (inflx. ε 13,700), $\gamma_{max}$ (CHCl$_3$) 3300, 1780, 1740, 1710 (b), 1690 cm$^{-1}$; δ ppm (CDCl$_3$) 1.50 (s, 9H), 3.00 and 3.43 (ABq, 2H, J=19Hz), 3.53 and 4.18 (ABq, 2H, J=16Hz), 3.87 (s, 3H, OMe), 4.85 and 4.90 (s, 1H, 235 (ε 20,800), 265 (inflx. ε 13,200); $\nu_{max}$ (KBr) 1760, 1680 cm$^{-1}$

EXAMPLE 7

Preparation of 3-(p-Carboxybenzyl)-7β-[D-α-ureido-β-(3-indolyl)-propionamido] phenylacetamido-ceph-3-em-4-carboxylic acid (XXVI)

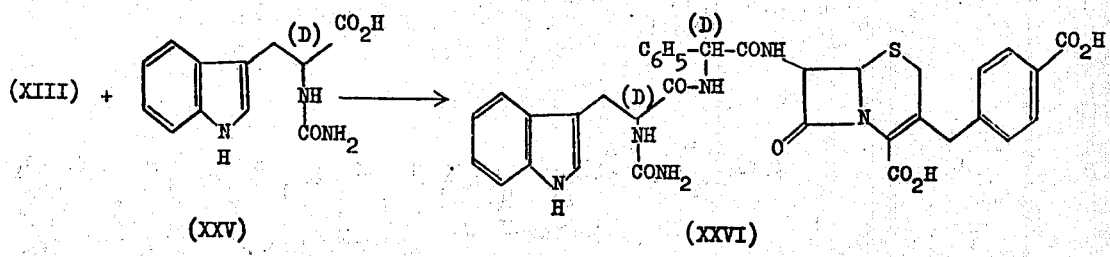

N-Carbamoyl-D-tryptophan (XXV) (0.1 g) and an equivalent amount of N-hydroxysuccinimide (47mg) in acetone (2.5 ml) and dimethylformamide (2.5 ml) was cooled to 0°. Dicyclohexylcarbodiimide (92 mg) was added and the mixture left stirring at 0° for 2½ hr, and then stored in the refrigerator overnight. The cephem (XIII) in water (1 ml) and acetone (1 ml) was treated with N-methylmorpholine (111 mg) to give a clear solution, which was cooled to 0°. The previously prepared active ester of (XXV) was filtered into this solution at 0°, after 0.5 hr. at this temperature the mixture was left at room temperature for 1½ hr. The acetone was removed under reduced pressure and the aqueous solution acidified with 2N HCl and the product (XXVI) (230 mg) filtered off, washed with a little acid then water and dried. $\nu_{max}$ (KBr) 1770, 1690–1650 (b) cm$^{-1}$.

The minimum inhibitory concentrations (MIC) of this compound required to inhibit the growth of various bacteria on nutrient agar are tabulated below:

| Gram-positive bacteria | MIC (μg/ml) |
| --- | --- |
| Staph. aureus Oxford | 0.5 |
| Staph. aureus Russell | 5.0 |
| Gram-negative bacteria | |
| E. coli JT1 | 5.0 |
| Salm. typhi | 5.0 |
| Shig. sonnei | 5.0 |
| Klebsiella aerogenes A | 5.0 |
| P. mirabilis C977 | 12.5 |

A solution of the aminocephem (XI) (0.32 g) in methylene chloride (5 ml) containing triethylamine (0.175 g) was cooled to −10°. A solution of DL-α-phenoxycarbonyl-3-thienylacetyl chloride (0.42 g) in methylene chloride (3 ml) was added over five minutes to the reaction mixture. The reaction mixture was stirred for a further 0.5 hr at −10°, and was then washed with water. Evaporation of the dried methylene chloride solution and chromatography of the residue on silica gel, eluting with ethylacetatepetroleum ether mixtures gave the cephem (XXVII) (317 mg) as a solid m.p. 138°–140° (chloroform-ether). $\nu_{max}$ (CHCl$_3$) 1780, 1710, 1690 cm$^{-1}$. δ ppm (CDCl$_3$) 1.52 (s, 9H), 3.02 and 3.5 (ABq, 2H, J=18Hz.), 3.54 and 4.18 (ABq, 2H, J=14Hz), 3.86 (s, 3H), 5.0 (s, 1H), 5.02 (d, 1H, J=5Hz), 5.35 (s, 2H), 5.88 (dd, 1H, J=5, 9Hz), 6.9–7.66 (m, 9H), 8.1 (d, 2H). (Found: C, 63.52; H, 5.18; N, 3.5; S, 8.48%. C$_{40}$H$_{38}$ N$_2$O$_9$S$_2$ requires: C, 63.7; H, 5.03; N, 3.71; S, 8.48%).

(b) Preparation of
7β-(DL-α-phenoxycarbonyl-3-thienylacetamido)-3-(p-carboxybenzyl)ceph-3-em-4-carboxylic acid (XXVIII).

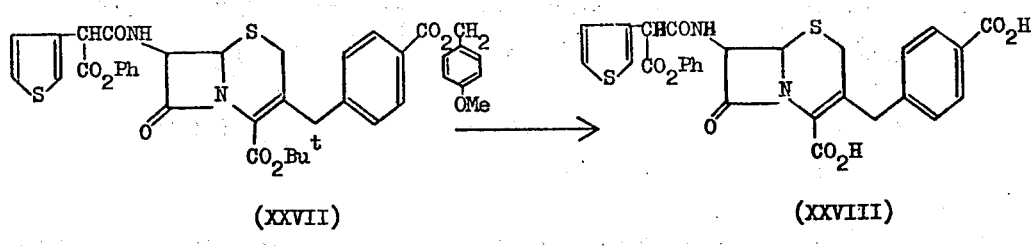

(XXVII) → (XXVIII)

EXAMPLE 8

(a) Preparation of t-Butyl
7β-(DL-α-phenoxycarbonyl-3-thienylacetamido)-3-[p(p-methoxybenzyloxycarbonyl)benzyl]ceph-3-em-4-carboxylate (XXVII)

The cephem (XXVII) (220 mg) was dissolved in trifluoroacetic acid (2 ml) and the solution was kept at room temperature for 10 minutes. The solution was evaporated and the residual gum re-evaporated from dry toluene (3 × 5 ml). The gum was triturated with dry ether to give the desired cephem (XXVIII) (132 mg). $\nu_{max}$ (KBr) 1760, 1690, 1650 cm$^{-1}$.

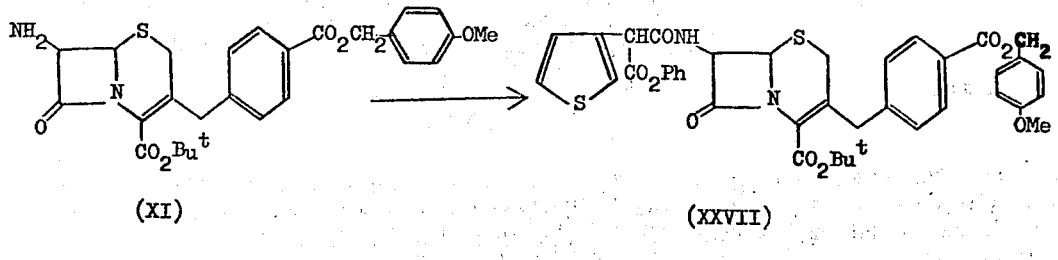

(XI) → (XXVII)

EXAMPLE 9

(a) Preparation of t-Butyl 7β-(2-thienylacetamido)-3-[p(p-methoxybenzyloxy carbonyl)benzyl]ceph-3-em-4-carboxylate (XXIX)

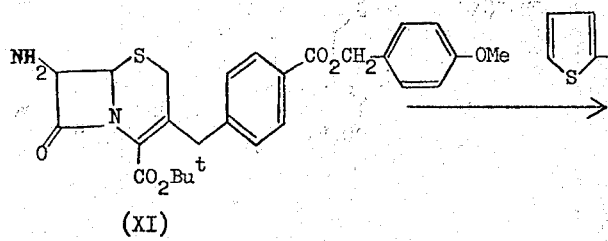 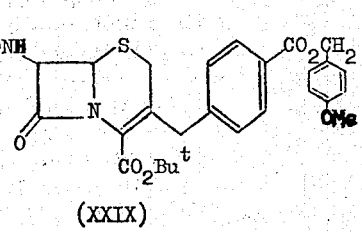

A solution of 2-thienylacetyl chloride (80 mg) in methylene chloride (1 ml) was added to a cooled (−10°) solution of the amino cephem (XI) (250 mg) in methylene chloride (10 ml) containing triethylamine (55mg). The reaction mixture was stirred for 1 hr at −20° and was then washed with water. Evaporation of the dried methylene chloride solution and chromatography of the residue on silica gel, eluting with ethyl acetate-petroleum ether mixtures, gave the cephem (255 mg) as a solid. $\nu_{max}$ (CHCl$_3$) 3300, 1780, 1710, 1680 cm$^{-1}$; δ ppm (CDCl$_3$) 1.56 (s, 9H), 3.0 and 3.44 (ABq, 2H, J=18Hz), 3.5 and 4.12 (ABq, 2H, J=14Hz), 3.94 (s, 5H), 5.02 (d, 1H, J=5Hz), 5.48 (s, 2H), 4.88 (dd, 1H, J=5 and 10Hz), 6.5 (d, 1H, J=9Hz), 6.98-7.62 (m, 9H), 8.1 (d, 2H, J=9Hz).

(b) Preparation of 7β-(2-Thienylacetamido)-3-(p-carboxybenzyl)ceph-3-em-4-carboxylic acid (XXX)

to give the desired cephem (XXX) (87 mg). $\nu_{max}$ (KBr) 1760, 1690, 1650 cm$^{-1}$ The minimum inhibitory concentrations (MIC) of this compound required to inhibit the growth of various bacteria on nutrient agar are tabulated below:

| Gram-negative bacteria | MIC (μg/ml) |
|---|---|
| *Salm. typhi* | 5.0 |
| *P. mirabilis* C977 | 5.0 |
| *P. mirabilis* 899 | 2.5 |
| Gram-positive bacteria | |
| *Staph. aureus* Oxford | 0.1 |
| *Staph. aureus* Russell | 5.0 |
| β-*Haemolytic Strep.* CN10 | 0.5 |
| *B. subtilis* | 1.2 |

EXAMPLE 10

(a) t-Butyl 3-[m-(p-methoxybenzyloxycarbonyl)benzyl]-7β-(N-t-butoxycarbonyl-D-α-phenylglycyl)amino-ceph-3-em-4-carboxylate (XL)

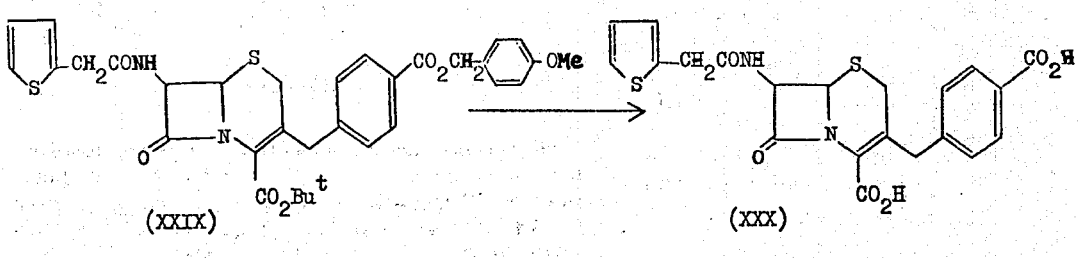

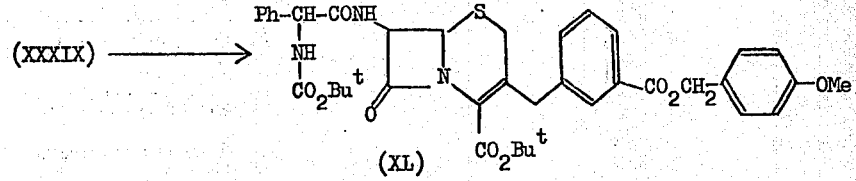

The cephem (XXIX) (150 mg) was dissolved in trifluoroacetic acid (5 ml) and the solution was kept at room temperature for 10 minutes. The solution was evaporated and the residual gum re-evaporated from dry tolune (3×5 ml). The gum was triturated with ether The protected cephem (XXXIX) (0.42 g prepared as described later) in methylene chloride (3 ml) was cooled to −20°. Toluene-p-sulphonic acid monohydrate (104 mg) in the minimum of methanol was added and the mixture left in the refrigerator overnight. The reaction was diluted with ethyl acetate, washed with NaHCO₃ solution, water, dried and evaporated. The residual gum (0.424 g) containing the 7β-amino cephem and trityl alcohol was used without further purification. Acylation of this free base with the mixed anhydride from N-(t-butoxycarbonyl)-D-α-phenylglycine and methylchloroformate as in example 1 gave the protected cephem (XL) (70% from tritylamino), m.p. 109°–111°; $\lambda_{max}$ (EtOH) 269 nm (ε 12,040); $\nu_{max}$ (CHCl₃) 3340, 1780, 1710, 1690, 1610 cm⁻¹; δ ppm (CDCl₃) 1.38 (s, 9H), 1.51 (s, 9H), 2.91 and 3.31 (ABq, 2H, J=18Hz), 3.55 and 4.05 (ABq, 2H, J=16Hz), 3.81 (s, 3H), 4.88 (d, 1H, J=5Hz), 5.31 (s, 2H, partially covering d, 1H, d-CH), 5.85 (dd, 1H, J=5Hz, 10Hz), 6.8–8.7 (Ar, NH).

(b) Preparation of 3-(m-Carboxybenzyl)-7β-(D-α-phenylglycyl)amino-ceph-3-em-4-carboxylic acid (XLI)

(XL) ⟶

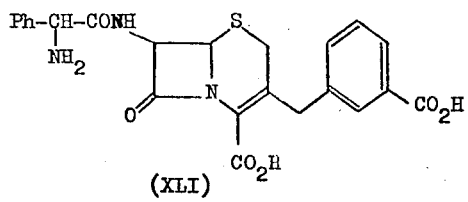

(XLI)

The cephem (XL) (0.245 g) was dissolved in trifluoroacetic acid (2 ml) and left at room temperature for 15 minutes. Work up as for (XIII, example 1) gave (XLI) (185 mg) as an amorphous solid, $\lambda_{max}$ (EtOH) 265 nm (ε 9,200); $\nu_{max}$ (KBr) 1770, 1690 (b) cm⁻¹.

The minimum inhibitory concentrations (MIC) of this compound required to inhibit the growth of various bacteria on nutrient agar are tabulated below:

| Gram-positive bacteria | MIC (μg/ml) |
|---|---|
| B. subtilis | 0.25 |
| Staph. aureus Oxford | 0.25 |
| Staph. aureus Russell | 1.25 |
| β-Haemolytic Strep. CN10 | 0.12 |
| Gram-negative bacteria | |
| E. coli JT1 | 12.5 |
| Salm. typhi | 2.5 |
| Klebsiella aerogenes A | 2.5 |
| P. mirabilis C977 | 2.5 |

EXAMPLE 11

(a) Preparation of t-Butyl 3-[m-(p-methoxybenzyloxycarbonyl)benzyl]-7β-(D-mandelyl)amino-ceph-3-em-4-carboxylate (XLII)

(XXXIX) ⟶

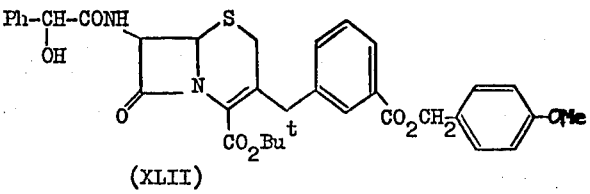

(XLII)

D-Mandelyl O-carboxyanhydride (80 mg) in methylene chloride (3 ml) was added to the cephem free base (100 mg, prepared as for example 10) in methylene chloride at −20°. After 2 hr at −20° the product (XLII) (105 mg) was isolated as in example 2, $\lambda_{max}$ (EtOH) 270 nm (ε 10,200); $\nu_{max}$ (CHCl₃) 3300, 1780, 1710, 1680, 1610 cm⁻¹; δ ppm (CDCl₃) 1.50 (s, 3H), 2.93 and 3.33 (ABq, 2H, J=19H), 3.80 (s, 3H), 3.50 and 4.03 (ABq, 2H, J=14Hz), 4.30 (bs, 1H, exch. D₂O), 4.88 (d, 1H, J=5Hz), 5.05 (s, 1H), 5.26 (s, 2H), 5.33 (dd, 1H, J=5Hz, 9Hz), 6.8–8.0 (Ar, 13H).

(b) 3-(m-Carboxybenzyl-7β-(D-mandelyl)amino-ceph-3-em-4-carboxylic acid (XLIII)

(XLII) ⟶

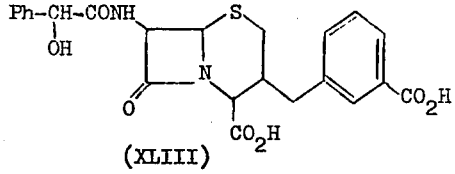

(XLIII)

The protected cephem (XLII) (82 mg) was dissolved in trifluoroacetic acid (1 ml) and left at room temperature for 20 minutes. Work up as in example 2 gave (XLIII) (60 mg) as an amorphous solid, $\lambda_{max}$ (EtOH) 267 (ε 6770), $\nu_{max}$ (KBr) 1770, 1690 cm⁻¹.

The minimum inhibitory concentrations (MIC) of this compound required to inhibit the growth of various bacteria on nutrient agar are tabulated below:

| Gram-positive bacteria | MIC (μg/ml) |
|---|---|
| B. subtilis | 0.5 |
| Staph. aureus Oxford | 0.5 |
| β-Haemolytic Strep. CN10 | 2.0 |
| Gram-negative bacteria | |
| Salm. typhi | 8.0 |
| P. mirabilis C977 | 8.0 |

PREPARATION OF STARTING MATERIAL FOR EXAMPLES 10 AND 11

(a) Preparation of 1-Bromo-[3-m-(p-methoxybenzyloxycarbonyl)phenyl-prop-2-yne] (XXXII)

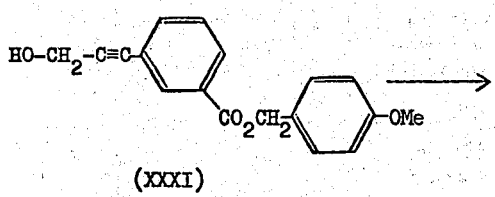

(XXXI)

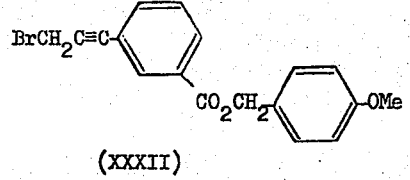

(XXXII)

The alcohol (XXXI) (10 g) in dry benzene (10 ml) was treated with triphenylphosphine (9.74 g) and carbon tetrabromide (12.3 g) as for (1). The product (12 g), m.p. 37°–40° showed $\nu_{max}$ (CHCl$_3$) 1720 cm$^{-1}$; δ ppm (CDCl$_3$) 3.76 (s, 3H), 4.12 (s, 2H), 5.12 (s, 2H), 6.9–8.2 (m, Ar, 8H).

(b) Preparation of
1-(1-Benzyloxycarbonyl-2-methyl-1-propenyl)-3-(triphenylmethylamino)-4-[3-m-(p-methoxybenzyloxycarbonyl)phenylprop-2-ynylthio] azetidin-2-one (XXXIII)

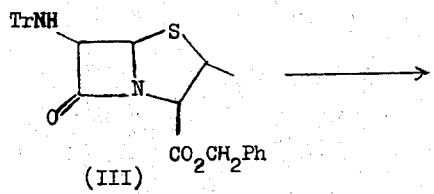

(III)

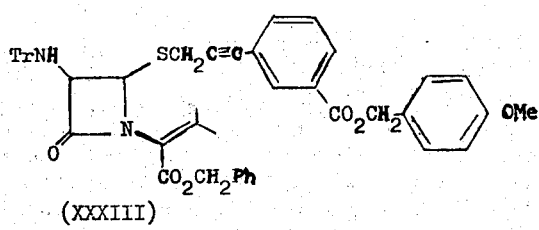

(XXXIII)

Benzyl 6β-(triphenylmethylamino)penicillanate (16 g) was stirred in dry tetrahydrofuran (160 ml) containing the bromide (XXXII) (12 g) and powdered sodium hydroxide (1.4 g) at room temperature for 24 hr. Work up as for the preparation of (IV) gave (XXXIII) (18 g) as a foam, $\nu_{max}$ (CHCl$_3$) 1765, 1720, 1620 cm$^{-1}$; δ ppm (CDCl$_3$) 2.00 (s, 3H), 2.15 (s, 3H), 2.76 and 3.10 (ABq, 2H, J=17Hz, covering exchangeable NH signal), 3.78 (s, 3H), 4.58 (bs, 1H, collapsing to d, J=5Hz on D$_2$O exch.), 4.90 (d, 1H, J=5Hz), 4.85 and 5.09 (ABq, 2H, J=12Hz), 5.30 (s, 2H), 6.8–8.1 Ar, 28H).

(c) Preparation of
3-(Triphenylmethylamino)-4-[3-m-(p-methoxybenzyloxycarbonyl)phenylprop-2-ynylthio]azetidin-2-one (XXXV)

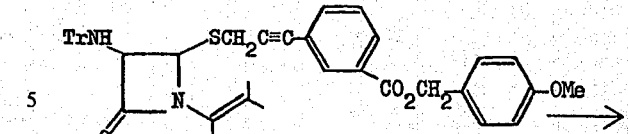

(XXXIV)

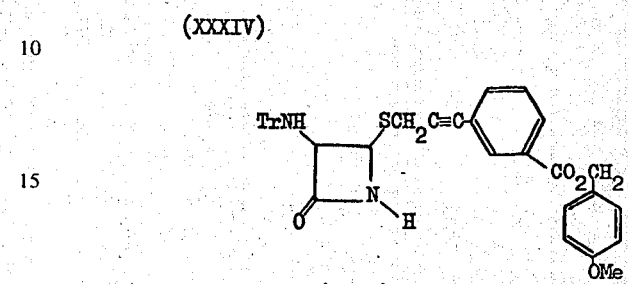

(XXXV)

The seco-derivative (XXXIV) (18 g) in dimethylformamide (54 ml), pyridine (54 ml) and water (11 ml), was cooled to −20° (bath temp). Powdered potassium permanganate was added portionwise and the mixture stirred for 1 hr at −20°. Work up as for the preparation of (V) gave the azetidinone (XXXV) (3.55 g.) as an amorphous solid, $\nu_{max}$ (CHCl$_3$) 3430, 1720 cm$^{-1}$; δ ppm (CDCl$_3$) 3.20 (s, 2H, covering exch. 1H signal), 3.75 (s, 3H), 4.55 (bs, 2H collapsing to singlet on D$_2$O exch. β-lactam protons), 5.29 (s, 2H), 6.74 (bs, 1H, exch), 6.8–8.1 (m, Az, 23H).

(d) Preparation of
1-(1-Hydroxy-1-t-butoxycarbonylmethyl)-3-(triphenylmethylamino)-4-[3-m-(p-methoxybenzyloxycarbonyl)phenylprop-2-ynythio]azetidin-2-one (XXXVI)

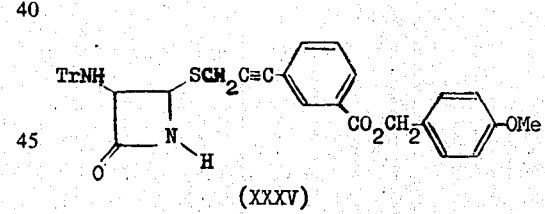

(XXXV)

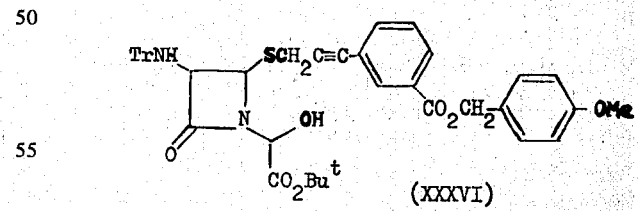

(XXXVI)

The azetidinone (XXXV) (5 g) was reacted with t-butyl glyoxylate (9g) as for the preparation of (VI). The product (5 g) was obtained as a foam, $\nu_{max}$ (CHCl$_3$) 3550, 1775, 1730 cm$^{-1}$.

(e) Preparation of
1-(1-t-Butoxycarbonyl-1-triphenylphosphoranylidenemethyl)-3-(triphenylmethylamino)-4-[3-m-(p-methoxybenzyloxycarbonyl)phenylprop-2-ynylthio]azetidin-2-one. (XXXVII)

(XXXVI) ⟶

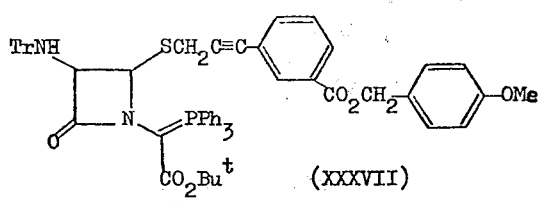
(XXXVII)

The alcohol (XXXVI) (5.0 g) in dry tetrahydrofuran (50 ml) was treated with lutidine (2.38 g) and thionyl chloride (2.33 g) as for the preparation of (VII). The chloride obtained (4.0 g) was dissolved in dry dioxan (50 ml) and treated with triphenylphosphine (2.7 g) and lutidine (1.1 g) at 50° for 15 hr. Work up an chromatography as for (VIII) gave (XXXVII) (4.45 g), $\nu_{max}$ (CHCl$_3$) 1760, 1720, 1640, 1620 cm$^{-1}$.

(f) Preparation of
1-(1-t-Butoxycarbonyl-1-triphenylphos-phoranylidenemethyl)-3-(triphenylmethylamino)-4-[3-m-(p-methoxybenzyloxycarbonyl)phenyl-2-oxo-propylthio]azetidin-2-one (XXXVIII)

(XXXVII) ⟶

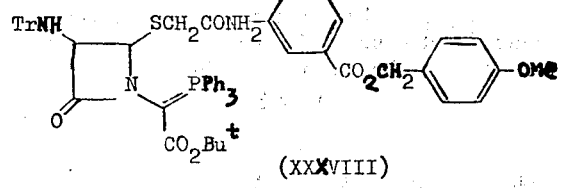
(XXXVIII)

The phosphorane (XXXVII) (4 g) in piperidine (25 ml) was refluxed for 5½ hr under nitrogen. The reaction was worked up and the ketone (XXXVIII) (3.01 g), isolated as for (IX), $\nu_{max}$ (CHCl$_3$) 1750, 1710, 1630, 1610 cm$^{-1}$.

(g) Preparation of t-Butyl
3-[m-(p-methoxybenzyloxycarbonyl)benzyl]-7β-(triphenylmethylamino) ceph-3-em-4-caboxylate (XXXIX)

(XXXVIII) ⟶

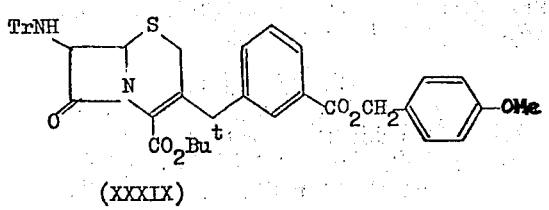
(XXXIX)

The keto-phosphorane (XXXVIII) (3 g) in dry dioxan (30 ml) was refluxed under nitrogen for 11 hr. The solution was evaporated to dryness and chromatographed to give the product (XXXIX) (1.52 g) which crystallised from chloroform-ether, m.p. 171°–172°; $\lambda_{max}$ (EtOH) 271 ($\epsilon$14,700); $\nu_{max}$ (CHCl$_3$) 1775, 1720, 1610 cm$^{-1}$; δ ppm (CDCl$_3$), 1.50, (s, 9H), 2.95 (d, 1H, J=9Hz exch. D$_2$O), 2.83 and 3.20 (ABq, 2H, J=18Hz), 3.51 and 3.98 (ABq, 2H, J=14Hz), 3.78 (s, 3H), 4.28 (d, 1H, J=5Hz), 4.75 (dd, 1H, J=5Hz, 9Hz collapsing to d J=5Hz on D$_2$O exch.), 5.30 (s, 2H), 6.83–8.0 (Ar, 23H).(Found: C, 73.1; H, 6.0; N, 3.6; S, 4.3. C$_{46}$H$_{44}$N$_2$O$_6$S requires, C, 73.4; H, 5.9; N, 3.7; S, 4.3%).

EXAMPLE 12

(a) Preparation of t-Butyl
3-[o-(p-methoxybenzyloxycarbonyl)benzyl]-7β-(N-t-butoxycarbonyl-D-α-phenylglycyl-)amino-ceph-3-em-4-carboxylate (LIV)

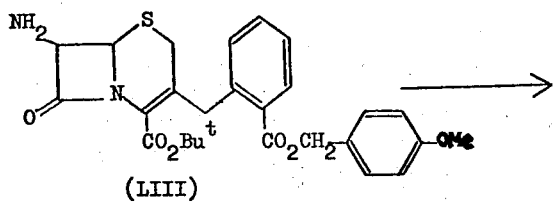
(LIII)

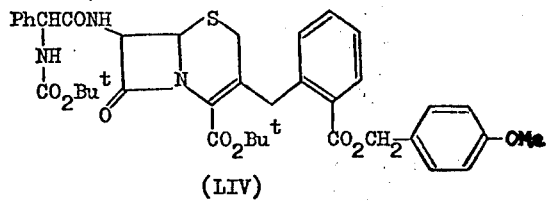
(LIV)

Treatment of the amino cephem (LIII) (0.75 g), with the mixed anhydride produced by treatment of N-(t-butoxycarbonyl)D-α-phenylglycine (0.4 g) with methyl chloroformate (0.15 g) in the presence of triethylamine (0.16 g), by the procedure used to prepare (XII), gave the required cephem (LIV) in 60% yield as a solid m.p. 157°–159°, $\nu_{max}$ (CHCl$_3$) 3300, 1770, 1700 cm$^{-1}$; δ ppm (CDCl$_3$) 1.4 (s, 9H), 1.48 (s, 9H), 2.96 and 3.34 (2H, ABq, J=19Hz), 3.9 (s, 3H), 4.24 (s, 2H), 4.87 (d, 1H, J=5Hz), 5.32 (m, 3H), 5.8 (m, 2H), 6.5 (1H), 6.98 (d, 2H, J=9Hz), 7.2–8.0 (m, 11H). (Found:- C, 64.90; H, 6.30; N, 5.50; S, 4.52%. C$_{40}$H$_{45}$N$_3$O$_9$S requires: C, 64.60; H, 6.05; N, 5.65; S, 4.30%).

(b) Preparation of
3-(o-Carboxybenzyl)-7β-(D-α-phenylglycyl-)aminoceph-3-em-4-carboxylic acid (LV)

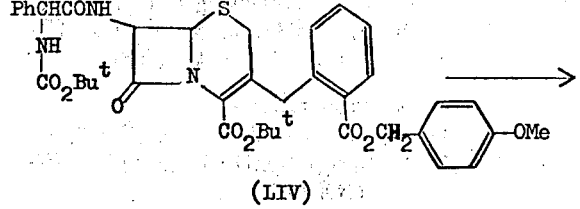
(LIV)

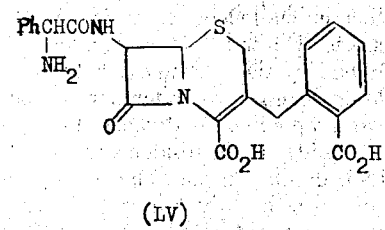

(LV)

The cephem (LIV) (150 mg) was dissolved in trifluoroacetic acid (1 ml) and the solution was kept at room temperature for 10 minutes. The solution was evaporated and the residual gum re-evaporated from dry toluene (3 × 5 ml). Trituration of the residual gum with dry ether gave the desired cephem (LV) (92 mg., 80%) as the trifluoroacetic acid salt. $\nu_{max}$ (Nujol) 1760, 1680 cm$^{-1}$.

The minimum inhibitory concentrations of this compound required to inhibit the growth of various bacteria on nutrient agar are tabulated below:

| Gram-negative bacteria | MIC ($\mu$g/ml) |
|---|---|
| E. coli JT1 | 12.5 |
| Klebsiella aerogenes A | 5.0 |
| P. mirabilis C977 | 5.0 |
| P. mirabilis 889 | 5.0 |
| Gram-positive bacteria | |
| B. subtilis | 1.25 |
| Staph. aureus Oxford | 5.0 |
| β-Haemolytic Strep. CN10 | 5.0 |

EXAMPLE 13

(a) Preparation of t-Butyl 3-[o-(p-methoxybenzyloxycarbonyl)benzyl]-7β-(N-t-butoxycarbonyl-DL-α-amino-2-thienylacetamido)-3-cephem-4-carboxylate (LVI)

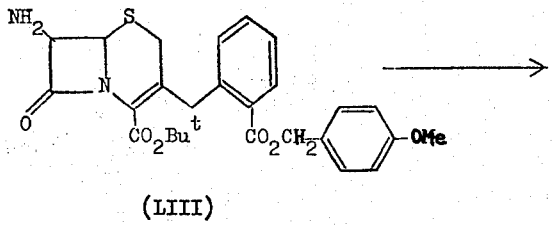

(LIII)

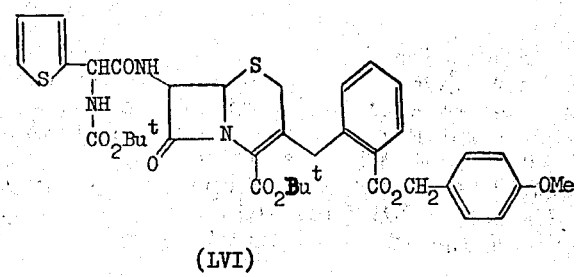

(LVI)

A solution containing triethylamine (22 mg), n-)t-butoxycarbonyl)-DL-α-amino-2-thienylacetic acid (55 mg), and N,N-dimethylbenzylamine (1 microdrop), in dry tetrahydrofuran (2 ml) was added dropwise over 5 minutes to a stirred solution of methyl chloroformate (21 mg) in dry tetrahydrofuran (0.5 ml) at −10°. The mixture was stirred for a further 0.5 hr at −20° before a solution of the amino cephem (LIII) (100 mg) in dry tetrahydrofuran (2 ml) was added dropwise over 5 minutes. After stirring for a further 2 hr at −20° the solution was diluted with ethyl acetate and washed successively with dilute hydrochloric acid (0.25 N, 10 ml) the water, and saturated sodium bicarbonate solution. Evaporation of the dried ethyl acetate layer and chromatography of the residue on silica gel, eluting with ethyl acetate/petroleum ether mixtures gave the cephem (LVI) (132 mg, 90%) as a crisp foam; $\nu_{max}$ (CHCl$_3$) 3300, 1775, 1710, 1610 cm$^{-1}$; δ ppm (CDCl$_3$) 1.48 (s, 9H), 1.54 (s, 9H), 3.2 (m, 2H), 3.9 (s, 3H), 4.22 (s, 2H), 4.86 (d, 1H, J=5Hz), 5.28 (s, 2H), 5.5–5.9 (m, 3H), 6.8–8.0 (m, 12H). (Found: M 749; C$_{38}$H$_{43}$N$_3$O$_9$S$_2$ requires M 749).

(b) Preparation of 3-(o-Carboxybenzyl)-7β-(DL-α-amino-2-thienylacetamido)-3-cephem-4-carboxylic acid (LVII)

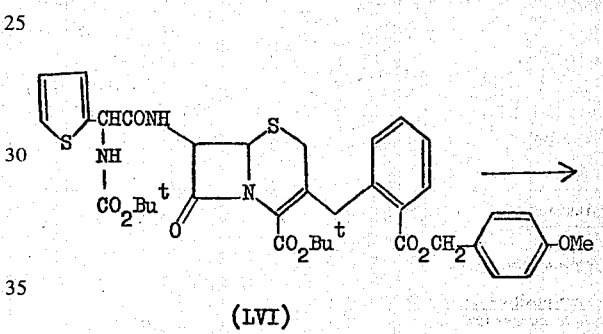

(LVI)

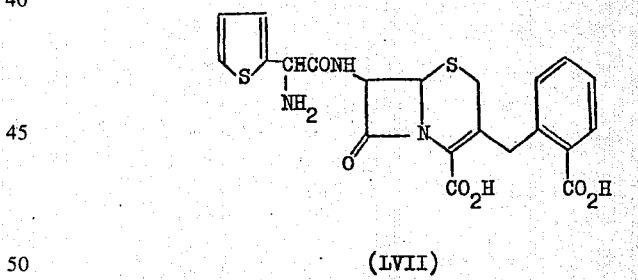

(LVII)

The cephem (LVI) (78 mg) was dissolved in trifluoroacetic acid (0.5 ml) and the solution was kept at room temperature for 10 minutes. The solution was evaporated and the residual gum re-evaporated from dry toluene (3×5 ml). Trituration of the residual gum with dry ether gave the required cephem (LVII) (48 mg., 97%) as the trifluoroacetic acid salt; $\nu_{max}$ (Nujol) 1770 cm$^{-1}$.

EXAMPLE 14

Pareparation of 3-(o-Carboxybenzyl)-7β-[D-α-(3-cinnamoul-3-methylureido) phenylacetamido]ceph-3-em-4-carboxylic acid (LVIX)

(LV) +

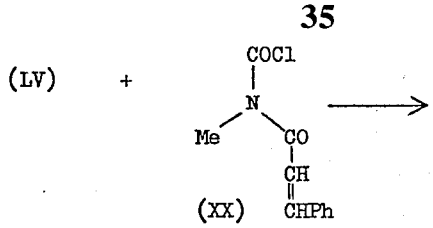

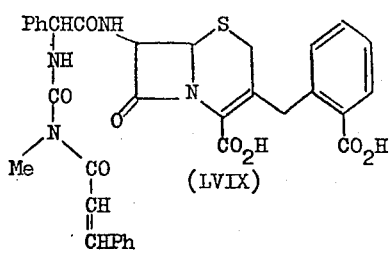

The cephem (LV) (0.162 g of the trifluoroacetic acid salt) was treated with triethylamine (112 mg) and the carbamoyl chloride (XX) (62 mg) as in the preparation of (XXI). The product (LVIX) (0.1 g) was obtained as a white solid; $\nu_{max}$ (CHCL$_3$) 3200, 1770, 1690 cm$^{-1}$.

The minimum inhibitory concentrations (MIC) of this compound required to inhibit the growth of various bacteria on nutrient agar are tabulated below:

| Gram-negative bacteria | MIC (μg/ml) |
|---|---|
| Shig. sonnei | 4.0 |
| Serratia marcescens US32 | 4.0 |
| Gram-positive bacteria | |
| Staph. aureus Oxford | 4.0 |
| β-haemolytic Strep. CN10 | 0.25 |

EXAMPLE 15

Preparation of 3-(o-Carboxybenzyl)-7β-[D-α-(3-benzylideneimino-3-methylureido)-phenylacetamido]-ceph-3-em-4-carboxylic acid (LVIII)

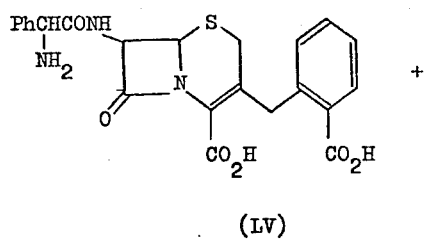

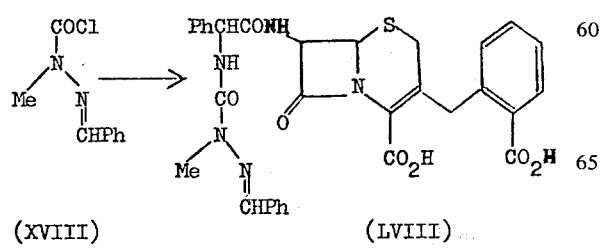

The cephem (LV) (0.162 g as the trifluoroacetic acid salt) in methylene chloride (5 ml) was stirred and cooled (ice-bath). Triethylamine (112 mg) was added folloed by the carbamoyl chloride (XVIII) (53 mg). After stirring at room temperature for 3 hr the solution was evaporated to dryness. Ethyl acetate and water were added to the residue and the pH adjusted to 2 with 1N hydrochloric acid. The ethyl acetate layer was separated, washed with water, dried and evaporated. The residue was triturated with ether, filtered, and collected to give (LVIII) (0.1 g) as a white solid $\nu_{max}$ (CHCl$_3$) 3200, 1770, 1680 (b) cm$^{-1}$.

The minimum concentrations (MIC) of this compound required to inhibit the growth of various bacteria on nutrient agar are tabulated below:

| Gram-negative bacteria | MIC (μg/ml) |
|---|---|
| Shig. sonnei | 4.0 |
| E. coli JT1 | 8.0 |
| Enterobacter cloacae N1 | 8.0 |
| Gram-positive bacteria | |
| β-haemolytic Strep. CN10 | 0.2 |
| Staph. aureus Oxford | 8.0 |

PREPARATION OF STARTING MATERIAL FOR EXAMPLES 12, 13, 14 AND 15

(a) Preparation of 1-Bromo-[3-o-(p-methoxybenzyloxycarbonyl)]phenyl-prop-2-yne (XLV)

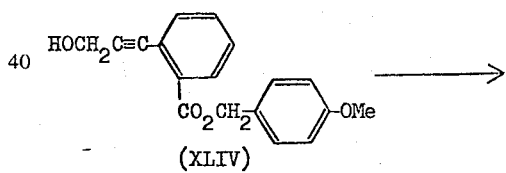

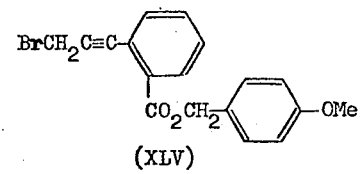

The bromide (XLV) was prepared by reaction of the alcohol (XLIV) (11.4 g) with triphenylphosphine (11.4 g) and carbon tetrabromide (12.74 g) in benzene (25 ml) according to the preparation of (II). The bromide (11.0 g, 80%) was obtained as an oil, $\nu_{max}$ (CHCl$_3$) 1720, 1620 cm$^{-1}$; δ ppm (CDCl$_3$) 3.85 (s, 3H), 4.05 (s, 2H), 5.4 (s, 2H), 6.98 (d, 2H, J=9Hz), 7.3–7.65 (m, 5H), 7.9–8.1 (m,1H).

(b) Preparation of (1-(1-Benzyloxycarbonyl-2-methyl-1-propenyl)-3(triphenylmethylamino)-4-[3-o(p-methoxybenzyloxycarbonyl)phenylprop-2-ynylthio]azetidin-2-one (XLVI)

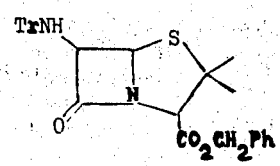

(III)

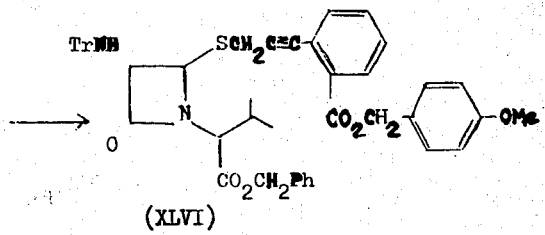

(XLVI)

The seco-penicillin (XLVI) was prepared by reaction of benzyl 6β-triphenylmethylamino)penicillanate (III) (2.74 g), the bromide (XLV) (2.0 g) and sodium hydroxide (0.28 g) in tetrahydrofuran, by the method used to prepare (IV). The product (2.5 g, 65%) was obtained as an amorphous solid $\nu_{max}$ (CHCL$_3$) 1760, 1720, 1620 cm$^{-1}$; δ ppm (CDCl$_3$) 2.0 (s, 3H), 2.15 (s, 3H), 2.95 (bs, 2H, covering exchangeable NH signal 1H), 3.82 (s, 3H), 4.6 (dd, 1H, J=5 and 10Hz collapses to d, J=5Hz on D$_2$O exchange), 4.98 (s, 2H), 5.05 (d, 1H, J=5Hz), 5.28 (s, 2H), 6.90 (d, 2H, J=9Hz), 7.1–7.6 (m, 25H), 7.8–8.1 (m, 1H).

(c) Preparation of
3-(Triphenylmethylamino)-4-[3-o(p-methoxybenzyloxycarbonyl) phenylprop-2-ynylthio]azetidin-2-one (XLVII)

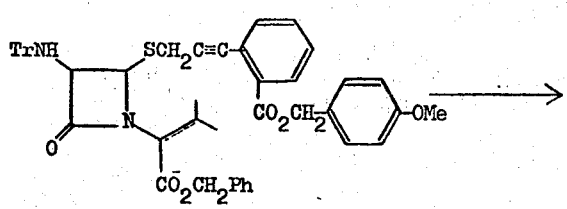

(XLVI)

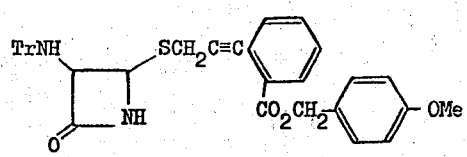

(XLVII)

The azetidinone (XLVII) was prepared by oxidation of 1-(1-benzyloxycarbonyl-2-methyl-1-propenyl)-3-(triphenylmethylamino)-4-[3-o(p-methoxybenzyloxycarbonyl)phenylprop-2-ynylthio]azetidin-2-one (XLVI) (2.5 g) according to the procedure used to prepare (V). The product (xLVII) (0.48 g., 25%) was obtained as an amorphous solid, $\nu_{max}$ (CHCl$_3$) 3250, 1760, 1710 cm$^{-1}$; δ ppm (CDCl$_3$) 3.0 (d, 1H, J=8Hz., NH exchanges with D$_2$O), 3.4 (s, 2H), 3.8 (s, 3H), 4.63 (bs, 2H), 5.26 (s, 2H), 6.8–8.1 (m, 24H).

(d) Preparation of
1-(1-Hydroxy-1-t-butoxycarbonylmethyl)-3-(triphenylmethylamino)-4-[3-o-(methoxybenzyloxycarbonyl)phenylprop-2-ynylthio]azetidin-2-one (XLVIII)

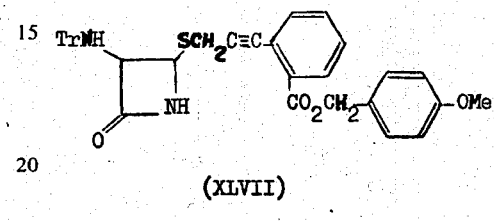

(XLVII)

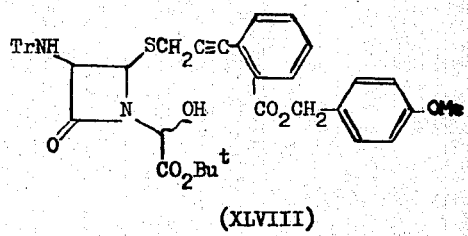

(XLVIII)

The alcohols (XLVIII) were prepared from the azetidinone (XLVII) (11.5 g.) and t-butyl glyoxylate (25 g) by refluxing in benzene, as in the preparation of alcohols (VI). The alcohols (XLVIII) (10.7 g., 80%) were obtained as an amorphous solid $\nu_{max}$ (CHCl$_3$) 3500, 1765, 1730 cm$^{-1}$; δ ppm (CDCl$_3$) 1.45 (s, 9H), 3.0–3.3 (m, 2H, covering exchangeable NH signal), 3.82 (s, 3H), 4.1–4.8 (m, 2H, 1H exchanges with D$_2$O), 5.0–5.35 (m, 2H), 5.3 (s, 2H), 6.8–8.15 (m, 23H).

(e) Preparation of
1-(1-Chloro-1-t-butoxycarbonylmethyl)-3-(triphenylmethylamino)-4-[3-o-(p-methoxybenzyloxycarbonyl)-phenylprop-2-ynylthio]azetidin-2-one (XLVIX)

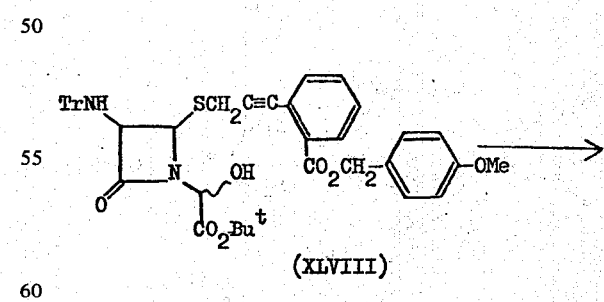

(XLVIII)

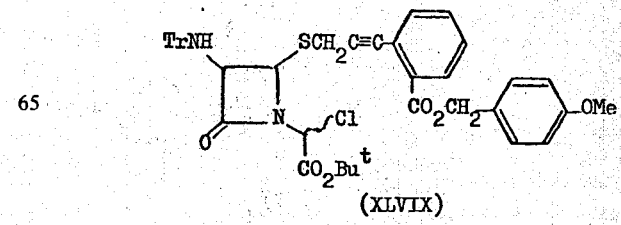

(XLVIX)

The chlorides (XLVIX) were prepared by reaction of the alcohols (XLVIII) (10.74 g) with thionyl chloride (5 g) in the presence of lutidine (3.6 g) in tetrahydrofuran, as in the preparation of (VII). The chlorides (8.0 g) were obtained as a foam $\nu_{max}$ (CHCl$_3$) 1770, 1740 cm$^{-1}$.

(f) Preparation of 1-(1-t-Butoxycarbonyl-1-triphenylphosphoranylidenemethyl)-3-(triphenylmethylamino)-4-[3-o-(p-methoxybenzyloxycarbonyl)phenylprop-2-ynylthio]azetidin-2-one (L)

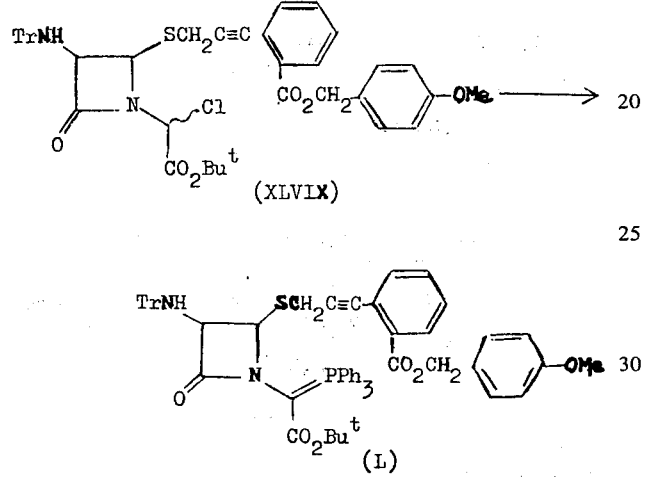

The phosphorane (L) was prepared from the chlorides (XLVIX) (8 g) by reaction with triphenylphosphine (7.15 g) in the presence of lutidine (2.5 g) in dioxan, according the preparation of (VIII). The phosphorane (6.7 g, 50%) was isolated as an a morphous solid $\nu_{max}$ (CHCl$_3$) 1750, 1720 cm$^{-1}$.

(g) Preparation of 1-(1-t-Butoxycarbonyl-1-triphenylphosphoranylidenemethyl)-3-(triphenylmethylamino)-4-[3-o-(p-methoxybenzyloxycarbonyl)phenyl-2-oxopropylthio]azetidin-2-one (LI)

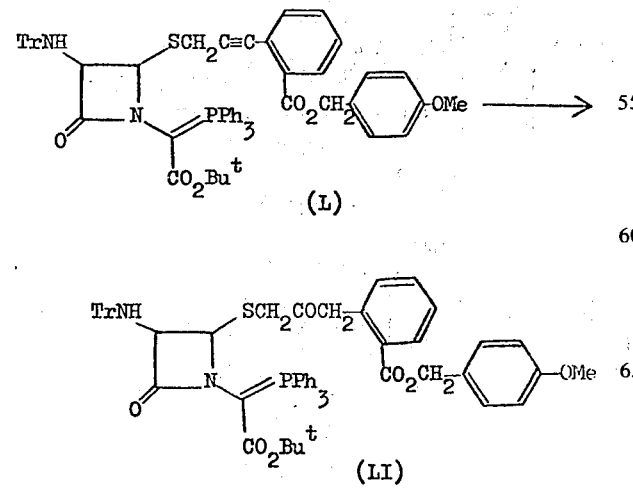

The keto-phosphorane (LI) was prepared from the phosphorane (L) (6.7 g) by treatment with piperidine according to the preparation of (IX). The ketophosphorane (6.16 g, 90%) was isolated as an amorphous solid $\nu_{max}$ (CHCl$_3$) 1740, 1710, 1620 cm$^{-1}$.

(h) Preparation of t-Butyl-3-[o-(p-methoxybenzyloxycarbonyl)benzyl]-7-triphenylmethylamino-ceph-3-em-4-carboxylate (LII)

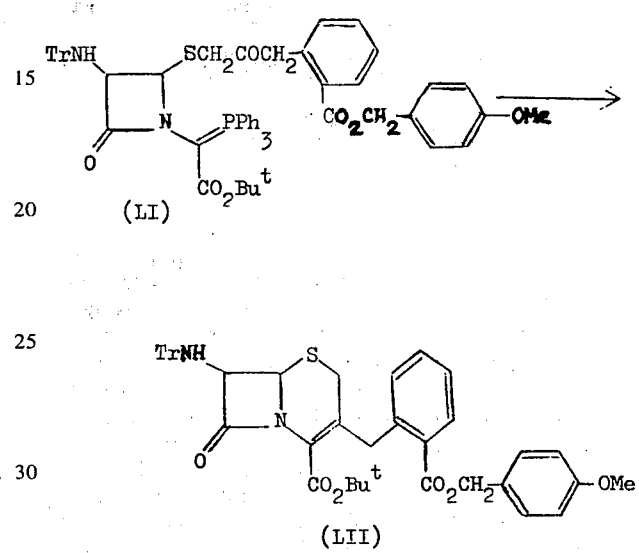

The trityl cephem (LII) was prepared from the keto-phosphorane (LI) (6.16 g) by boiling under reflux in dioxan, according to the preparation of (X). The cephem (2.9 g) was isolated as needles m.p. 210°–211° (chloroform-methanol), $\nu_{max}$ (CHCl$_3$) 1775, 1710 cm$^{-1}$; $\gamma$ ppm (CDCl$_3$) 1.48 (s, 9H), 2.98 (m, 2H), 3.8 (s, 3H), 4.17 (m, 3H), 4.72 (dd, 1H, J=5Hz and 10 Hz), 5.30 (s, 2H), 6.7–7.9 (m, 23H).

(i) Preparation of t-Butyl 3-[o-(p-methoxybenzyloxycarbonyl)benzyl]-7-aminoceph-3-em-4-carboxylate (LIII)

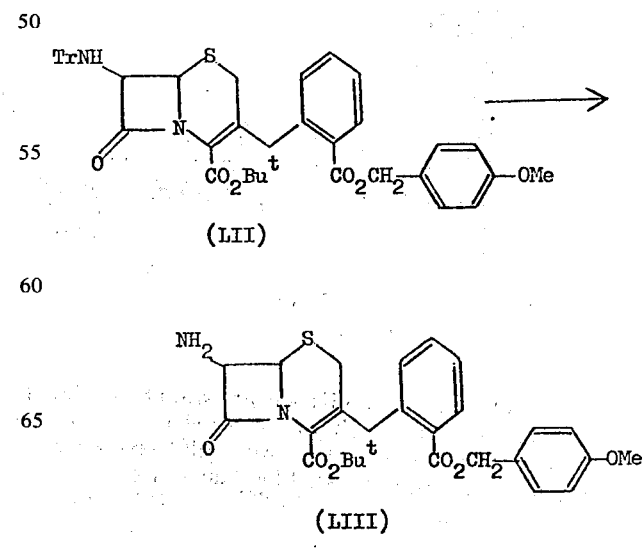

Treatment of a solution of the trityl cephem (LII) (2 g) in methylene chloride (20 ml) with p-toluene sulphonic acid (0.55 g) in methanol (5 ml) as in the preparation of (XI), gave the amino cephem (LIII) as an amorphous solid $\nu_{max}$ (CHCl$_3$) 3400, 1775, 1710 cm$^{-1}$; δ ppm (CDCl$_3$) 1.48 (s, 9H), 1.70 (s, 2H), 3.15 and 3.2 (2H, inner signals of ABq), 3.82 (s, 3H), 4.18 (s, 2H), 4.68 (d, 1H, J=5Hz), 4.88 (d, 1H, J=5Hz), 5.38 (s, 2H), 6.90 (d, 2H, J=9Hz), 7.2-8.0 (m, 6H).

EXAMPLE 16

(a) Preparation of t-Butyl 3[3,5-di-(p-methoxybenzyloxycarbonyl)benzyl]-7β-(N-t-butoxycarbonyl-D-α-phenylglycyl)amino-ceph-3-em-4-carboxylate (LXVI)

(LXV) 

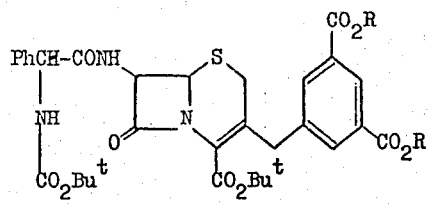

(LXVI)   (R= p-methoxybenzyl)

The free base (LXV) (367 mg) was acylated with the mixed anhydride from N-(t-butoxycarbonyl)-D-α-phenylglycine (150 mg) and methyl chloroformate (57 mg) as in example 1. Work up and chromatography gave the cephem (LXVI) (286 mg) as an amorphous solid, $\nu_{max}$ (CHCl$_3$) 3500, 3400, 1785, 1720–1690 (b) cm$^{-1}$, δ ppm (CDCl$_3$) 1.38 (s, 9H), 1.50 (s, 9H), 2.92 and 3.33 (ABq, 2H, J=18Hz), 3.64 and 4.09 (ABq, 2H, J=15Hz), 3.98 (s, 6H), 4.90 (d, 1H, J=5Hz), 5.22 (d, 1H, J=6Hz), 5.32 (s, 4H), 5.68 (d, 1H, J=6Hz), 5.80 (dd, 1H, J=5Hz; 9Hz, collapsing to d J=5Hz on D$_2$O exch.), 6.65 (d, 1H, J=9Hz exch. with D$_2$O), 6.92 (d, 4H, J=8Hz), 7.30 (s, 5H), 7.40 (d, 4H, J=8Hz), 8.11 (m, 2H), 8.58 (m, 1H). (Found: C, 64.5; H, 5.9; N, 4.6; S, 3.9%, C$_{49}$H$_{53}$N$_3$O$_{12}$S requires C, 64.8; H, 5.9; N, 4.6; S, 3.5%).

(b) Preparation of 3-(3,5-dicarboxybenzyl)7β-(D-α-phenylglycyl)aminoceph-3-em-4-carboxylic acid (LXII)

(LXVI) 

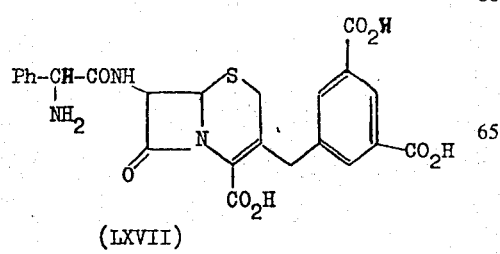

(LXVII)

Deprotection of (LXVI) with trifluoroacetic acid for 30 min at room temperature followed by isolation as in example 1 gave the trifluoroacetic acid salt of (LXVII) as an amorphous solid, $\nu_{max}$ (EtOH) 260 nm (ε 6,800), $\nu_{max}$ (KBr) 1760, 1690 (b) cm$^{-1}$.

PREPARATION OF STARTING MATERIAL FOR EXAMPLE 16

(a) Preparation of 1-Bromo-3-[3,5-di-(p-methoxybenzyloxycarbonyl)-phenyl]prop-2-yne (LXI)

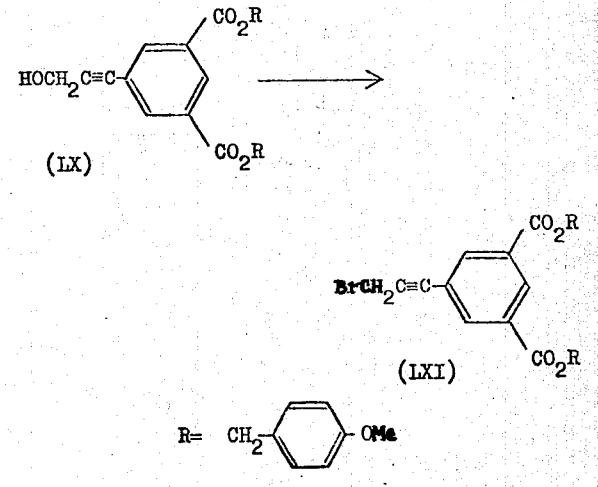

R= CH$_2$-⌬-OMe

Treatment of the alcohol (LX) with triphenylphosphine-carbon tetrabromide as for the preparation of (II) gave the bromide (LXI), m.p. 83°–86°, $\nu_{max}$ (CHCl$_3$) 1720 cm$^{-1}$; δ ppm (CDCl$_3$) 3.85 (s, 6H), 4.17 (s, 2H), 5.37 (s, 4H), 6.98 (4H, d, J=9.5Hz), 7.47 (d, 4H, J=9.5Hz), 8.35 (m, 2H), 8.75 (m, 1H), (b) Preparation of 1-(1-Benzyloxycarbonyl-2-methyl-1-propenyl)-3-(triphenylmethylamino)-4-[3-(3,5-di-p-methoxybenzyloxycarbonylphenyl)-prop-2-ynylthio]azetidin-2-one (LXII)

(III) 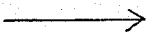

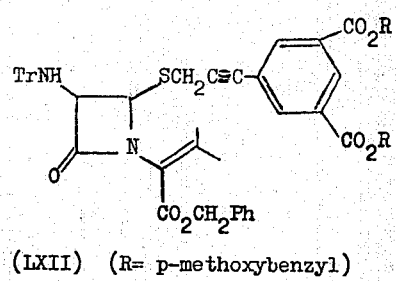

(LXII)   (R= p-methoxybenzyl)

Reaction of benzyl 6-β-(triphenylmethylamino)-penicillanate (III) with the bromide (LXI) as in the preparation of (IV) gave the secopenicillin (LXII, 65%) as an amorphous solid, $\nu_{max}$ (CHCl$_3$) 1760, 1720, 1615 cm$^{-1}$; δ ppm (CDCl$_3$) 1.99 (s, 3H), 2.13 (s, 3H), 2.75 and 3.09 (ABq, 2H, J=17Hz covering exch. NH signal), 3.77 (s, 6H), 4.56 (m, 1H, collapsing to d, J=5Hz on D$_2$O exch.), 4.87 (d, 1H, J=5Hz), 4.83 and 5.08 (ABq, 2H, J=12Hz), 5.30 (s, 4H), 6.75–8.67 (Ar, 31H). (Found: C, 73.8; H, 5.7; N, 2.8. C$_{61}$H$_{54}$N$_2$O$_9$S requires C, 73.9; H, 5.5; N, 2.8%).

(c) Preparation of 3-(Triphenylmethylamino)-4-[3-(3,5-di-p-methoxybenzyloxycarbonylphenyl)prop-2-ynylthio]azetidin-2-one (LXIII)

(LXII) 

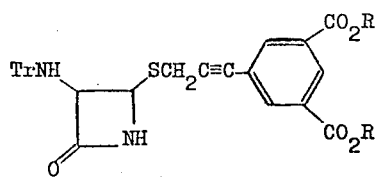

(LXIII) (R= p-methoxybenzyl)

Oxidation of (LXII) (DMF/pyridine/water/0°) in the manner described for previous examples gave the azetidinone (LXIII) as a foam, $\nu_{max}$ (CHCL$_3$) 1770, 1720 cm$^{-1}$; δ ppm (CDCl$_3$) 3.02 (bs, 1H, exch. D$_2$O), 3.22 (s, 2H), 3.78 (s, 6H), 4.58 (m, 2H, collapsing to singlet on D$_2$O exch. β-lactam protons), 5.28 (s, 4H), 6.23 (s, 1H, exch. D$_2$O), 6.78-8.67 (Ar).

(d) Preparation of t-Butyl 3-[3,5-di-(p-methoxybenzyloxycarbonyl)benzyl]-7β-(triphenylmethylamino) ceph-3-em-4-carboxylate (LXIV)

(LXIII) 

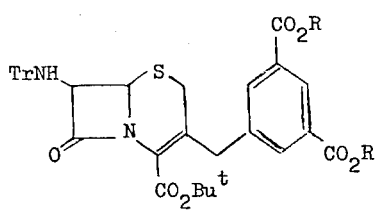

(LXIV) (R= p-methoxybenzyl).

The azetidinone (LXIII) was converted into the cephem (LXIV) as for the sequence (V) (VI) (VII) (VIII) (IX) (X)

The final product (LXIV) was obtained as a foam, $\nu_{max}$ (CHCl$_3$) 1780, 1720 cm$^{-1}$ δ ppm (CDCl$_3$) 1.47 (s, 9H), 2.85–3.10 (m, 3H, 1H exch., leaving inner signals of ABq at δ 2.95 and 3.05), 3.82 (s, 6H, partially obscured ABq of 2H), 4.27 (d, 1H, J=4.5Hz), 4.72 (dd, J=4.5, 10Hz, collapsing to d, J=4.5Hz, on D$_2$O exch.), 5.32 (s, 4H), 6.83–8.63 (Ar, 26H).

(e) Preparation of t-butyl 3-[3,5-di(p-methoxybenzyloxycarbonyl]-7β-aminoceph-3-em-4-carboxylate (LXV)

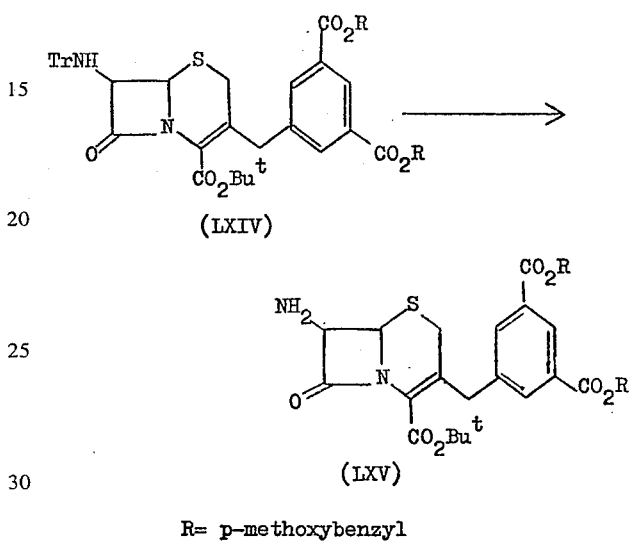

R= p-methoxybenzyl

The cephem (LXIV) (183 mg) in methylene chloride (5 ml) was cooled (−20°) and treated with toluene-p-sulphonic acid (42 mg) in the minimum volume of methanol. After standing overnight in the refrigerator the solution was dissolved in ethyl acetate and washed with sodium bicarbonate solution, dried and evaporated. Chromatography of the residue gave the product (LXV) (70 mg, 52%) as a foam, $\lambda_{max}$ (EtOH) 229 nm (ε 30,400), 276 nm (ε 8,300); $\nu_{max}$ 3500, 3400, 1780, 1720 cm$^{-1}$; δ ppm (CDCl$_3$) 1.50 (s, 9H), 1.78 (bs, 2H, exch. D$_2$O), 3.00 and 3.43 (ABq, 2H, J=18Hz), 3.81 (s, 6H, obscurring ABq, 2H), 4.71 (d, 1H, J=5Hz), 4.94 (d, 1H, J=5Hz), 5.32 (s, 4H), 6.90 (d, 4H, J=8Hz), 7.38 (d, 4H, J=8Hz), 8.13 (2H), 8.60 (m, 1H).

EXAMPLE 17

Serum Concentrations of 3-(Carboxybenzyl)cephems

In addition to having valuable antibacterial activity, some of the new cephems of this invention possess the added advantage that, when injected into the animal body, therapeutically useful concentrations of antibiotic are maintained in the bloodstream for an exceptionally long time.

The following three cephems were studied in mice in comparison with cefazolin, which is itself regarded as a relatively 'long-acting' cephalosporin.

(D)

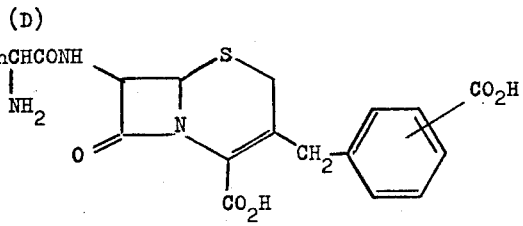

Each compound was injected sub-cutaneously into groups of mice at a dose of 50 mg/kg, and serum samples were taken at timed intervals thereafter and assayed microbiologically for their antibiotic content using the appropriate compound as standard. The following average data were obtained:

| Compound | Serum concentrations ($\mu g/ml$) at time after dosing | | | | | |
|---|---|---|---|---|---|---|
| | 10 min | 20 min | 30 min | 60 min | 2 hr | 4 hr |
| p-carboxy isomer | 75 | 87 | 69 | 48 | 22 | 9.3 |
| m-carboxy isomer | 84 | 64 | 50 | 26 | 14 | 1.6 |
| o-carboxy isomer | 63 | 66 | 58 | 49 | 41 | 31 |
| Cefazolin | 45 | 37 | 21 | <4 | <4 | <4 |

What I claim is:

1. A cephalosporin analogue of the formula (IV):

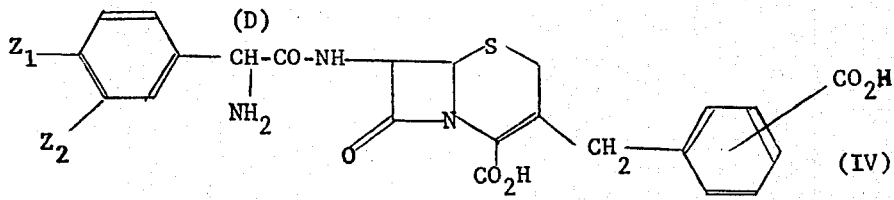

or a pharmaceutically acceptable salt thereof wherein $Z_1$ is hydrogen or hydroxyl and $Z_2$ is hydrogen or chlorine.

2. A compound according to claim 1 wherein $Z_2$ is hydrogen.

3. A compound according to claim 2 wherein $Z_1$ is hydrogen.

4. A salt of a compound according to claim 1 wherein the salt is the sodium, potassium, calcium, magnesium, aluminum or ammonium salt.

5. A salt of a compound according to claim 1 wherein the salt is the sodium or potassium salt.

6. The compound according to claim 1 which is 3-(o-carboxybenzyl)-7β-(D-α-phenylglycyl)amino-ceph-3-em-4-carboxylic acid.

7. The compound according to claim 1 which is 3-(m-carboxybenzyl)-7β-(D-α-phenylglycyl)amino-ceph-3-em-4-carboxylic acid.

8. The compound according to claim 1 which is 3-(p-carboxybenzyl)-7β-(D-α-phenylglycyl)amino-ceph-3-em-4-carboxylic acid.

9. A pharmaceutical composition useful for treating bacterial infections in humans and animals which comprises an anti-bacterially effective amount of a compound of claim 1 in combination with a pharmaceutically acceptable carrier.

10. A composition according to claim 9 wherein $Z_2$ is hydrogen.

11. A composition according to claim 10 wherein $Z_1$ is hydrogen.

12. A composition according to claim 10 wherein the compound is in the form of a salt selected from the group consisting of the sodium, potassium, calcium, magnesium, aluminum and ammonium salts.

13. A pharmaceutical composition according to claim 12 wherein the salt is the potassium or sodium salt.

14. A pharmaceutical composition according to claim 9 wherein the compound is 3-(o-carboxybenzyl)-7β-(D-α-phenylglycyl)amino-ceph-3-em-4-carboxylic acid.

15. A pharmaceutical composition according to claim 9 wherein the compound is 3-(m-carboxybenzyl)-7β-(D-α-phenyl-glycyl)amino-ceph-3-em-4-carboxylic acid.

16. A pharmaceutical composition according to claim 9 wherein the compound is 3-(p-carboxybenzyl)-7β-(D-α-phenylglycyl)amino-ceph-3-em-4-carboxylic acid.

17. A pharmaceutical composition according to claim 9 in injectable administration form.

18. A method of treating bacterial injections in humans and animals which comprises administering to a human or animal in need thereof an anti-bacterially effective amount of a compound of claim 1.

19. A method according to claim 18 wheren $Z_2$ is hydrogen.

20. A method according to claim 19 wherein $Z_1$ is hydrogen.

21. A method according to claim 18 wherein the compound is administered in the form of a salt selected from the group consisting of the sodium, potassium, calcium, magnesium, aluminum and ammonium salts.

22. A method according to claim 21 wherein the salt is the sodium or potassium salt.

23. A method according to claim 18 wherein the compound is 3-(o-carboxybenzyl)-7β-(D-α-phenylglycyl)amino-ceph-3-em-4-carboxylic acid.

24. A method according to claim 18 wherein the compound is 3-(m-carboxybenzyl)-7β-(D-α-phenylglycyl)amino-ceph-3-em-4-carboxylic acid.

25. A method according to claim 18 wherein the compound is 3-(p-carboxybenzyl)-7β-(D-α-phenylglycyl)amino-ceph-3-em-4-carboxylic acid.

26. A method according to claim 18 wherein the administration is by injection.

* * * * *